(12) United States Patent
Lecocke et al.

(10) Patent No.: US 11,789,003 B1
(45) Date of Patent: Oct. 17, 2023

(54) WATER CONTAMINATION DETECTION SYSTEM

(71) Applicant: UIPCO, LLC, San Antonio, TX (US)

(72) Inventors: Meredith Beveridge Lecocke, San Antonio, TX (US); Michael J. Maciolek, Boerne, TX (US); Robert Wiseman Simpson, Fair Oaks Ranch, TX (US); Daniel Christopher Bitsis, Jr., San Antonio, TX (US); Bobby Lawrence Mohs, San Antonio, TX (US); Manfred Amann, San Antonio, TX (US); Emily Margaret Gray, San Antonio, TX (US); Donnette Moncrief Brown, San Antonio, TX (US)

(73) Assignee: United Services Automobile Association (USAA), San Antonio, TX (US)

( * ) Notice: Subject to any disclaimer, the term of this patent is extended or adjusted under 35 U.S.C. 154(b) by 963 days.

(21) Appl. No.: 16/376,480

(22) Filed: Apr. 5, 2019

Related U.S. Application Data

(60) Provisional application No. 62/753,654, filed on Oct. 31, 2018.

(51) Int. Cl.
| | |
|---|---|
| *G01V 3/00* | (2006.01) |
| *G01N 33/18* | (2006.01) |
| *G01D 21/02* | (2006.01) |
| *G01D 9/28* | (2006.01) |
| *G06Q 50/26* | (2012.01) |
| *G01D 9/40* | (2006.01) |
| *B64C 39/02* | (2023.01) |
| *B64U 101/30* | (2023.01) |

(52) U.S. Cl.
CPC .............. *G01N 33/1826* (2013.01); *G01D 9/28* (2013.01); *G01D 9/40* (2013.01); *G01D 21/02* (2013.01); *G06Q 50/265* (2013.01); *B64C 39/024* (2013.01); *B64U 2101/30* (2023.01)

(58) Field of Classification Search
CPC ......... G01N 33/1826; G01D 9/28; G01D 9/40; G01D 21/02; G06Q 50/265; B64C 39/024; B64C 2201/123; B64C 2201/127
USPC ..................................... 340/425.5, 436, 438
See application file for complete search history.

(56) References Cited

U.S. PATENT DOCUMENTS

| | | | |
|---|---|---|---|
| 4,256,403 A * | 3/1981 | Powell ................ | G01N 21/431 356/73 |
| 9,576,309 B2 | 2/2017 | Bollman, IV | |
| 9,679,539 B1 | 6/2017 | Kamath et al. | |
| 9,773,398 B2 | 9/2017 | Abrahams et al. | |

(Continued)

OTHER PUBLICATIONS

Final Office Action mailed Aug. 2, 2022 in U.S. Appl. No. 16/376,649.

(Continued)

*Primary Examiner* — Tai T Nguyen
(74) *Attorney, Agent, or Firm* — Plumsea Law Group, LLC

(57) ABSTRACT

A water contamination detection system. The system may include a device processor; and a non-transitory computer readable medium including instructions executable by the device processor to perform the following steps: receiving information indicative of the presence of one or more contaminants in water within a geographic region; determining a characterization of water contamination within the geographic region; and sending information regarding water contamination to a plurality of users of the system.

20 Claims, 26 Drawing Sheets

(56) References Cited

U.S. PATENT DOCUMENTS

| | | | |
|---|---|---|---|
| 9,947,233 | B2 | 4/2018 | Cui et al. |
| 10,467,885 | B2 | 11/2019 | Trundle et al. |
| 10,635,903 | B1 | 4/2020 | Harvey |
| 10,807,591 | B1 | 10/2020 | Kentley-Klay et al. |
| 2002/0022909 | A1 | 2/2002 | Karem |
| 2003/0083786 | A1 | 5/2003 | Pietrowicz et al. |
| 2008/0045156 | A1* | 2/2008 | Sakhpara ............ G01N 33/0063 455/66.1 |
| 2010/0227582 | A1 | 9/2010 | Berry et al. |
| 2012/0039400 | A1 | 2/2012 | Rieken |
| 2012/0050524 | A1 | 3/2012 | Rinner et al. |
| 2012/0290152 | A1 | 11/2012 | Cheung et al. |
| 2013/0222369 | A1 | 8/2013 | Huston et al. |
| 2013/0268196 | A1 | 10/2013 | Dam |
| 2014/0316616 | A1 | 10/2014 | Kugelmass |
| 2015/0112773 | A1 | 4/2015 | Shahraray et al. |
| 2015/0140954 | A1 | 5/2015 | Maier et al. |
| 2015/0310275 | A1 | 10/2015 | Dong et al. |
| 2016/0356713 | A1* | 12/2016 | Chen et al. .......... B01D 35/143 |
| 2017/0061660 | A1 | 3/2017 | Gahn et al. |
| 2017/0083979 | A1 | 3/2017 | Winn et al. |
| 2017/0227509 | A1* | 8/2017 | Chang et al. ...... G01N 33/0031 |
| 2017/0353346 | A1 | 12/2017 | Pfeffer et al. |
| 2018/0114174 | A1 | 4/2018 | Boland et al. |
| 2018/0314995 | A1 | 11/2018 | Katz et al. |
| 2018/0322197 | A1 | 11/2018 | Hesterman |
| 2018/0327091 | A1 | 11/2018 | Burks et al. |
| 2019/0120640 | A1 | 4/2019 | Ho et al. |
| 2019/0303990 | A1 | 10/2019 | Quinn |
| 2019/0362523 | A1 | 11/2019 | Ngoi et al. |
| 2020/0034620 | A1 | 1/2020 | Lutterodt |
| 2021/0192629 | A1 | 6/2021 | Tofte et al. |

OTHER PUBLICATIONS

Final Office Action mailed Feb. 2, 2021 in U.S. Appl. No. 16/376,378.
Final Office Action mailed Jan. 28, 2022 for U.S. Appl. No. 16/376,550.
Final Office Action mailed Sep. 13, 2022 for U.S. Appl. No. 16/376,599.
Non-Final Office Action mailed Apr. 5, 2019 in U.S. Appl. No. 16/376,599.
Non-Final Office Action mailed Apr. 13, 2022 in U.S. Appl. No. 16/376,550.
Non-Final Office Action mailed Aug. 16, 2022 in U.S. Appl. No. 17/409,096.
Non-Final Office Action mailed Jan. 4, 2023 for U.S. Appl. No. 16/376,649.
Non-Final Office Action mailed Jan. 14, 2022 in U.S. Appl. No. 16/376,649.
Notice of Allowance mailed Oct. 27, 2022 for U.S. Appl. No. 17/409,096.
Notice of Allowance mailed Oct. 28, 2022 for U.S. Appl. No. 16/376,550.
Office Action mailed Jul. 22, 2020 in U.S. Appl. No. 16/376,378.
Office Action mailed Jun. 14, 2021 in U.S. Appl. No. 16/376,550.

* cited by examiner

WATER CONTAMINATION DETECTION SYSTEM

TECHNICAL FIELD

The present disclosure generally relates to post-disaster condition monitoring systems and, more particularly, to a water contamination detection system.

BACKGROUND

Following disasters, such as hurricanes, tornados, floods, etc., it can be difficult to assess the conditions in a disaster area. Disaster response can be better tailored to the conditions if the conditions are known.

There is a need in the art for a system and method that addresses the shortcomings discussed above. In particular, there is a need in the art for a disaster condition monitoring system.

SUMMARY

The present disclosure is directed to systems and methods for monitoring the conditions following a disaster. In some embodiments, the disclosed system may be configured to detect power outages. In some embodiments, the system may be configured to detect water contamination. In some embodiments, the system may be configured to collect data regarding post-disaster conditions from pre-existing networks. In some embodiments, the system may be configured to utilize crowd sourced imagery to determine post-disaster conditions. In some embodiments, the system may be configured to utilize drones to collect imagery to determine post-disaster conditions. Further, the disclosed system may include an app or website interface to enable users to upload imagery and/or volunteer the services of their personal drone.

In one aspect, the present disclosure is directed to a power outage detection system. The system may include a device processor; and a non-transitory computer readable medium including instructions executable by the device processor to perform the following steps: receiving information indicative of the status of electrical power at a plurality of locations within a geographic region; determining the status of electrical power in the geographic region based on the status of electrical power at the plurality of locations; and sending information regarding the status of electrical power to a plurality of users of the system.

In another aspect, the present disclosure is directed to a power outage detection system. The system may include a device processor; and a non-transitory computer readable medium including instructions executable by the device processor to perform the following steps: receiving information indicative of the status of electrical power at a plurality of locations within a geographic region; determining the status of electrical power in the geographic region based on the status of electrical power at the plurality of locations; determining a boundary of an area in which electrical power is unavailable; and preparing a map that illustrates the boundary.

In another aspect, the present disclosure is directed to a power outage detection system. The system may include a device processor; and a non-transitory computer readable medium including instructions executable by the device processor to perform the following steps: receiving information indicative of the status of electrical power at a plurality of locations within a geographic region; determining the status of electrical power in the geographic region based on the status of electrical power at the plurality of locations; determining that a user within the geographic region has electrical power available based the information received; and preparing a map that indicates that an area proximate to the user in the geographic region has electrical power available.

In another aspect, the present disclosure is directed to a water contamination detection system. The system may include a device processor; and a non-transitory computer readable medium including instructions executable by the device processor to perform the following steps: receiving information indicative of the presence of one or more contaminants in water within a geographic region; determining a characterization of water contamination within the geographic region; and sending information regarding water contamination to a plurality of users of the system.

In another aspect, the present disclosure is directed to a water contamination detection system. The system may include a device processor; and a non-transitory computer readable medium including instructions executable by the device processor to perform the following steps: receiving information indicative of the presence of one or more contaminants in water within a geographic region; determining a characterization of water contamination within the geographic region; and preparing a map indicating the location of contamination in the water in the geographic region.

In another aspect, the present disclosure is directed to a water contamination detection system. The system may include a device processor; and a non-transitory computer readable medium including instructions executable by the device processor to perform the following steps: receiving information indicative of the presence of one or more contaminants in a body of water within a geographic region; determining a characterization of water contamination within the geographic region; and sending information regarding water contamination to a plurality of users of the system.

In another aspect, the present disclosure is directed to a post-disaster conditions monitoring system. The system may include a device processor; and a non-transitory computer readable medium including instructions executable by the device processor to perform the following steps: receiving information from one or more pre-existing networks; determining conditions in a geographic region based on the information received from the one or more pre-existing networks; and preparing a map indicating the conditions within the geographic region.

In another aspect, the present disclosure is directed to a post-disaster conditions monitoring system. The system may include a device processor; and a non-transitory computer readable medium including instructions executable by the device processor to perform the following steps: receiving information from one or more pre-existing networks; determining conditions in a geographic region based on the information received from the one or more pre-existing networks; and sending information regarding the determined conditions to a third party associated with disaster response.

In another aspect, the present disclosure is directed to a post-disaster conditions monitoring system. The system may include a device processor; and a non-transitory computer readable medium including instructions executable by the device processor to perform the following steps: receiving information from one or more pre-existing networks; determining conditions in a geographic region based on the information received from the one or more pre-existing networks; and sending information regarding the determined conditions to one or more users of the system.

In another aspect, the present disclosure is directed to a post-disaster conditions monitoring system. The system may include a device processor; and a non-transitory computer readable medium including instructions executable by the device processor to perform the following steps: receiving a plurality of images from a plurality of personal devices in a geographic region; determining conditions in a geographic region based on the information received from the plurality of images; and preparing a map indicating the determined conditions within the geographic region.

In another aspect, the present disclosure is directed to a post-disaster conditions monitoring system. The system may include a device processor; and a non-transitory computer readable medium including instructions executable by the device processor to perform the following steps: receiving a plurality of images from a plurality of personal devices in a geographic region; determining conditions in a geographic region based on the information received from the plurality of images; determining, based on the images, locations where images are needed to complete the determination of conditions in the geographic region; and preparing a map identifying one or more locations where imagery is needed.

In another aspect, the present disclosure is directed to a post-disaster conditions monitoring system. The system may include a device processor; and a non-transitory computer readable medium including instructions executable by the device processor to perform the following steps: displaying information regarding locations where images are needed to complete a post-disaster conditions determination; selecting at least one location of the one or more locations where images are needed; uploading images of the at least one location; and sending the images to a conditions monitoring center.

In another aspect, the present disclosure is directed to a post-disaster conditions monitoring system. The system may include plurality of aircraft drones configured to take photographic images; a conditions monitoring center having a controller including a device processor and a non-transitory computer readable medium including instructions executable by the device processor to perform the following steps: receiving images from the plurality of aircraft drones in a geographic region; determining conditions in the geographic region based on the images received from the plurality of aircraft drones; and sending information regarding the determined conditions to one or more users of the system.

In another aspect, the present disclosure is directed to a post-disaster conditions monitoring system. The system may include device processor; and a non-transitory computer readable medium including instructions executable by the device processor to perform the following steps: selecting an option to volunteer the services of a personal drone; and sending a registration for the volunteer drone services to a conditions monitoring center.

In another aspect, the present disclosure is directed to a post-disaster conditions monitoring system. The system may include a plurality of land vehicle drones equipped with air quality sensors: a conditions monitoring center having a controller including a device processor and a non-transitory computer readable medium including instructions executable by the device processor to perform the following steps: receiving data from the air quality sensors; determining conditions in a geographic region based on the data received from the air quality sensors; and sending information regarding the determined conditions to one or more users of the system.

Other systems, methods, features, and advantages of the disclosure will be, or will become, apparent to one of ordinary skill in the art upon examination of the following figures and detailed description. It is intended that all such additional systems, methods, features, and advantages be included within this description and this summary, be within the scope of the disclosure, and be protected by the following claims.

BRIEF DESCRIPTION OF THE DRAWINGS

The invention can be better understood with reference to the following drawings and description. The components in the figures are not necessarily to scale, emphasis instead being placed upon illustrating the principles of the invention. Moreover, in the figures, like reference numerals designate corresponding parts throughout the different views.

DESCRIPTION OF EMBODIMENTS

The disclosed post-disaster condition monitoring systems may include several features for assessing the conditions in a disaster area, which may enable more effective, efficient, and prioritized disaster response. The disclosed systems may be configured to detect power outages and/or water contamination by collecting information from various sources. In some embodiments, the system may be configured to collect data regarding post-disaster conditions from pre-existing networks, such as traffic lights, and residential services, such as Internet service. In some embodiments, the system may be configured to utilize crowd sourced imagery, e.g., by collecting images from the smart phones of person in a disaster area in order to determine post-disaster conditions. These images may be combined and analyzed in order to provide a clear illustration of the conditions across the various regions of a disaster area. Similarly, in some embodiments, the system may be configured to utilize drones to collect imagery to determine post-disaster conditions. Further, the disclosed system may include an app or website interface to enable users to upload imagery and/or volunteer the services of their personal drone, as well as interact with a conditions monitoring center performing the analyses.

Figure 1:
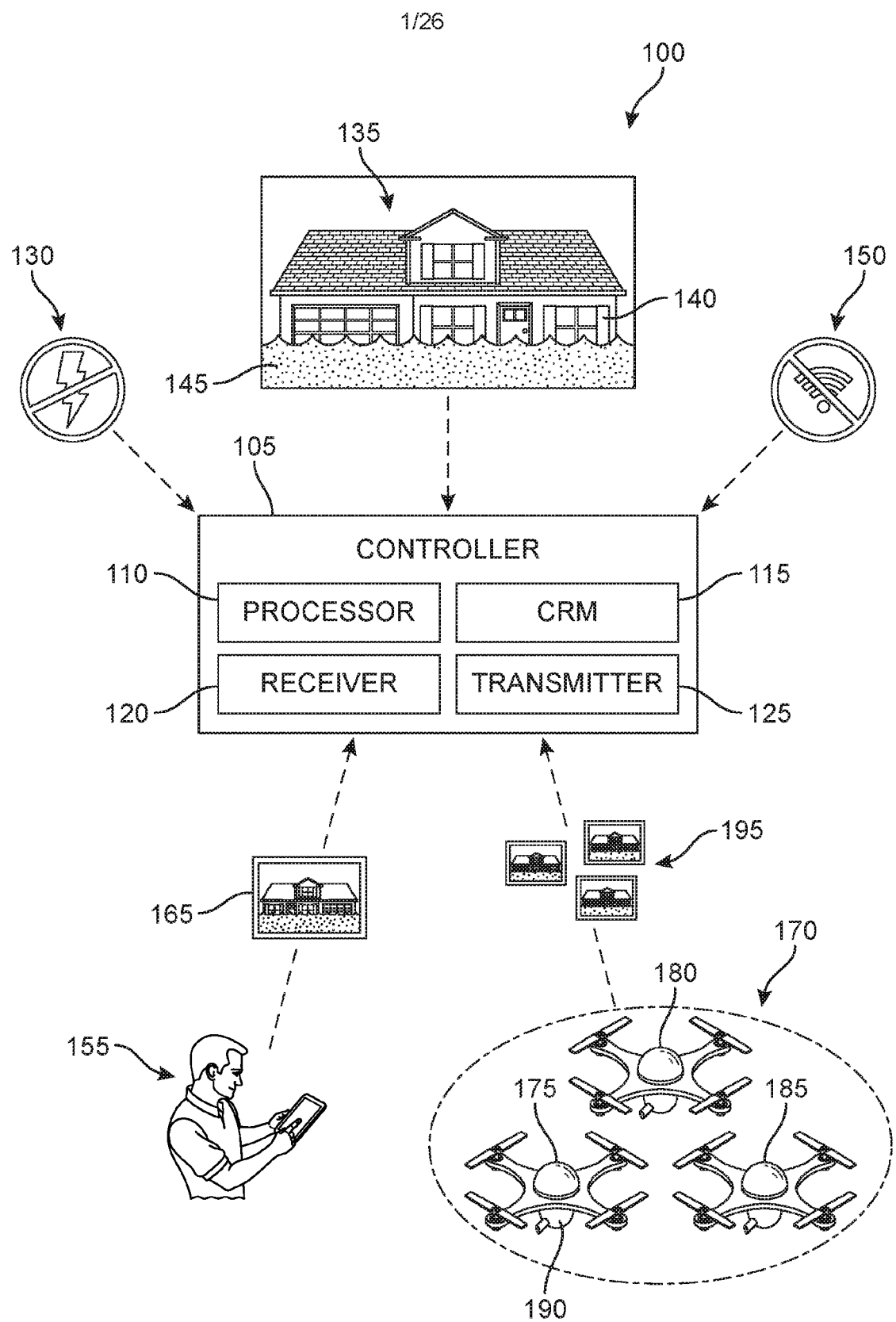
FIG. 1 is a schematic illustration of a disaster area monitoring system.

FIG. 1 is a schematic illustration of a disaster area monitoring system. As shown in FIG. 1, the disaster area monitoring system may include a power outage detection system 100. FIG. 1 is a schematic network illustration of system 100.

As shown in FIG. 1, system 100 may include a controller 105. Controller 105 may include various computing and communications hardware, such as servers, integrated circuits, displays, etc. Further, controller 105 may include a device processor 110 and a non-transitory computer readable medium 115 including instructions executable by device processor 110 to perform the processes discussed herein. The components of controller 105 may be implemented in association with a mobile conditions monitoring center, such as vehicle, or in association with a control center or conditions monitoring center located in a permanent building (i.e., brick and mortar establishment).

The non-transitory computer readable medium may include any suitable computer readable medium, such as a memory, e.g., RAM, ROM, flash memory, or any other type of memory known in the art. In some embodiments, the non-transitory computer readable medium may include, for example, an electronic storage device, a magnetic storage device, an optical storage device, an electromagnetic storage device, a semiconductor storage device, or any suitable combination of such devices. More specific examples of the non-transitory computer readable medium may include a portable computer diskette, a floppy disk, a hard disk, a read-only memory (ROM), a random access memory (RAM), a static random access memory (SRAM), a portable compact disc read-only memory (CD-ROM), an erasable programmable read-only memory (EPROM or Flash memory), a digital versatile disk (DVD), a memory stick, and any suitable combination of these exemplary media. A non-transitory computer readable medium, as used herein, is not to be construed as being transitory signals, such as radio waves or other freely propagating electromagnetic waves, electromagnetic waves propagating through a waveguide or other transmission media (e.g., light pulses passing through a fiber-optic cable), or electrical signals transmitted through a wire.

Instructions stored on the non-transitory computer readable medium for carrying out operations of the present invention may be instruction-set-architecture (ISA) instructions, assembler instructions, machine instructions, machine dependent instructions, microcode, firmware instructions, configuration data for integrated circuitry, state-setting data, or source code or object code written in any of one or more programming languages, including an object oriented programming language such as Smalltalk, C++, or suitable language, and procedural programming languages, such as the "C" programming language or similar programming languages.

Aspects of the present disclosure are described in association with figures illustrating flowcharts and/or block diagrams of methods, apparatus (systems), and computing products. It will be understood that each block of the flowcharts and/or block diagrams can be implemented by computer readable instructions. The flowcharts and block diagrams in the figures illustrate the architecture, functionality, and operation of possible implementations of various disclosed embodiments. Accordingly, each block in the flowchart or block diagrams may represent a module, segment, or portion of instructions. In some implementations, the functions set forth in the figures and claims may occur in an alternative order than listed and/or illustrated.

Controller 105 may include networking hardware configured to interface with other nodes of a network, such as a LAN, WLAN, or other networks. In Further, controller 105 may be configured to receive data from a plurality of sources and communicate information to one or more external destinations. Accordingly, controller 105 may include a receiver 120 and a transmitter 125. (It will be appreciated that, in some embodiments, the receiver and transmitter may be combined in a transceiver.)

Any suitable communication platforms and/or protocols may be utilized for communication between controller 105 and other components of the system. Since the various sources of information may each have their own platform and/or protocol, system 100 may be configured to interface with each platform and/or protocol to receive the data.

As shown in FIG. 1, system 100 may be configured to receive information regarding the conditions in a disaster area from a variety of sources. For example, as shown in FIG. 1, system 100 may receive electrical power outage information 130. In addition, system 100 may receive flooding information 135, as indicated in FIG. 1 by a house 140 with flood water 145. In some cases, contamination of the flood water may be detected. The stippling of flood water 145 indicates contamination of flood water 145 with any of a variety of contaminants.

As also shown in FIG. 1, system 100 may be configured to receive information regarding outages of residential services, such as Internet service 150. Knowledge of Internet outages enables disaster responders to identify whether Internet based communications are available to those who find themselves in a disaster area.

In some embodiments, system 100 may be configured to receive information reported by users. For example, as shown in FIG. 1, system 100 may be configured to receive information from a user 155. As an example, system 100 may be configured to receive photographic images 165 from user 155. Images of a disaster area enable a conditions monitoring center to make determinations regarding the best and most urgent way to respond to a disaster.

In some embodiments, system 100 may include a plurality of drones utilized to take photographic images of the disaster area. For example, as shown in FIG. 1, system 100 may be configured to receive information, such as photographic images of a disaster area from a fleet 170 of drones. Fleet 170 may include as many drones as suitable to monitor a disaster area of a given size and severity. FIG. 1 illustrates three such drones, including a first drone 175, a second drone 180, and a third drone 185. As shown in FIG. 1, these drones may be aerial drones. In some embodiments, land vehicle drones and/or watercraft drones may be used.

One or more of the drones may include photography equipment, such as a camera 190, as shown in FIG. 1. It will be understood that the drones disclosed herein may be capable of taking still images and/or video recordings. In some embodiments, the imaging may be more sophisticated. For example, in some cases the drones may be capable of infrared and/or night vision capabilities. As further shown in FIG. 1, controller 105 may be configured to receive images 195 from drone fleet 170. Accordingly, controller 105 may be configured to receive the various types of imagery that the drones are capable of obtaining. It will be understood that the other drones discussed below may also have a variety of data collection capabilities as set forth above.

The drones may be manually controlled or autonomously controlled. In some cases, controller 105 or another controller associated with the conditions monitoring center may communicate with the drones to control their operation and/or to receive the images taken by the drones. In some embodiments, a global positioning system (GPS) navigation system may be utilized to fly the drones to the desired location for taking photographs and back. For example, in some embodiments, the user may either input a location to which they would like the drone to fly. Alternatively, controller 105 may obtain location information recorded and transmitted by the user's personal electronic device. Controller 105 may be configured to dispatch and command the drones to complete reconnaissance flights to take images of a disaster area. Accordingly, computer readable medium 115 may include instructions for receiving this location information from any of a variety of sources and completing the drone mission to the designated location.

Information from other sources may be received by controller 105 in order to assess the conditions in a disaster area or any other area in which conditions are desired to be determined. For example, it may be desirable to monitor large crowds of people in order to maintain effective and efficient security and service among the crowd. Accordingly, system 100 may be utilized to monitor geographic regions and/or venues under circumstances other than disasters.

Based on the information received and processed by controller 105, system 100 may prepare a map illustrating conditions in the monitored geographic area. Information regarding multiple different conditions may be indicated on the map. In some embodiments, the information may be provided in layers. The layers may be selectable by the user as to which layers of information are shown on the map at a given time.

Figure 2:
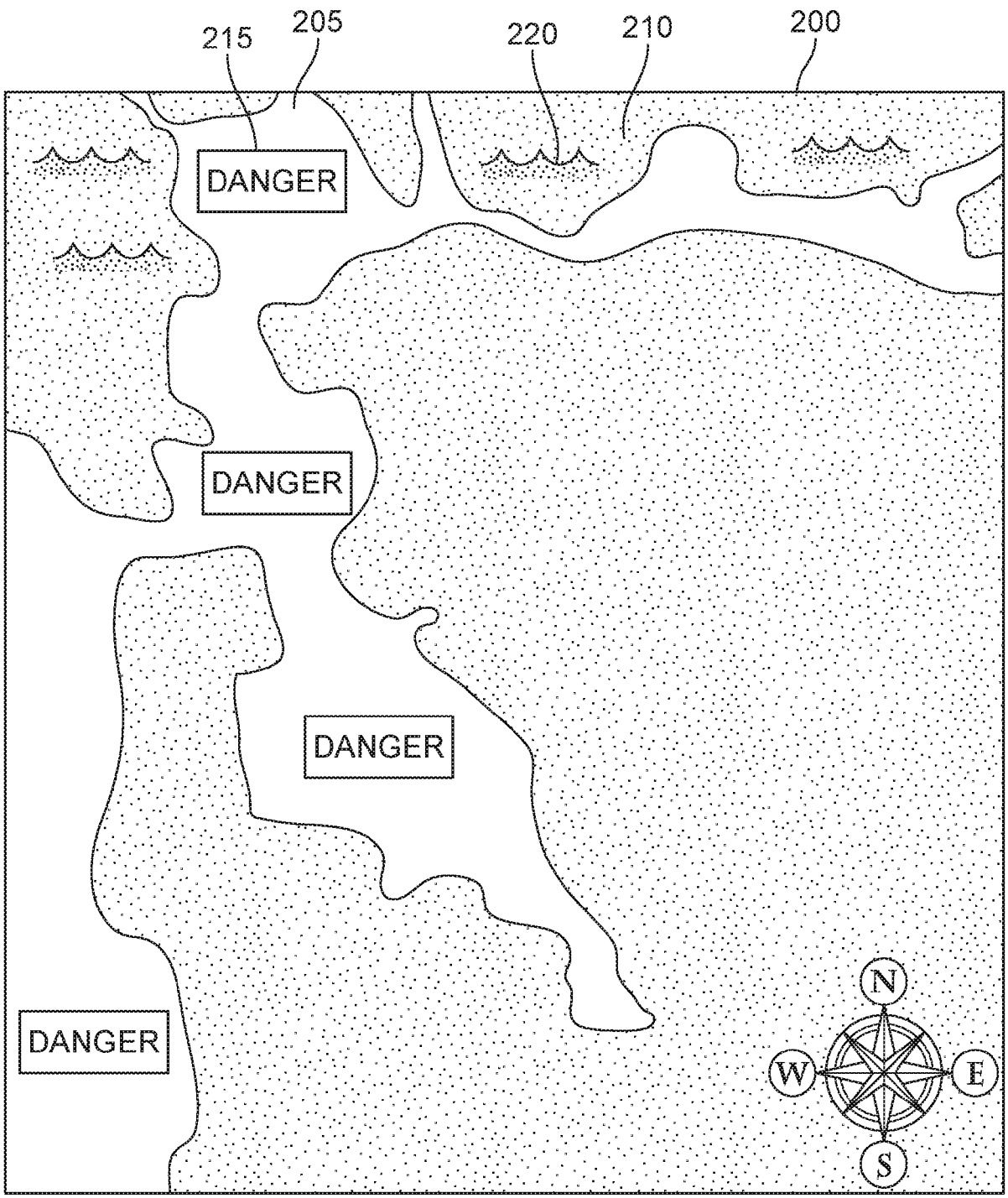
FIG. 2 is a schematic illustration of a map showing multiple layers of information illustrating different conditions within the disaster area.

FIG. 2 is a schematic illustration of a map showing multiple layers of information illustrating different conditions within the disaster area. As shown in FIG. 2, a map 200 illustrates a geographic region with land areas 205 and water areas 210. Map 200 shows at least two layers of post-disaster condition information. In particular, map 200 illustrates a plurality of areas 215 which have been determined to be dangerous. For example, these areas may include residential homes that have been severely damaged by a tornado, with debris littering the roadways in the area. In addition, map 200 also illustrates certain bodies of water to be contaminated, as indicated by symbol 220.

In some embodiments, either the "danger" layer or the water contamination layer of information may be deselected as desired. While map 200 is shown with only two layers for clarity, additional layers may be added. For example, other conditions for which alternative or additional layers could be added may include flooding, landslides, hail damage, flood damage, etc., as well as outages for various services, such as electrical power, landline telephone service, cellular (mobile phone and Internet) service, Wifi, etc.

Power Outages

A significant condition that dictates disaster response is the status of electrical power in a geographic region. In areas where select homes and buildings may be damaged by floods, fires, hurricanes, etc., some homes may be without electrical power, even though the electrical power grid as a whole in that area remains operational. That is, if a resident's home is damaged severely enough, they can lose electrical power even though the main power lines may be intact. Various other types of damage to buildings and their surroundings can cause power outages to select buildings in a geographic region.

The status of electrical power availability can be inferred based on several different sources of information. For example, if Internet of Things devices remain online and operational, it can be determined that at least one portion of that building has electrical power. Similarly, if residential services, such as Internet service, cable television, Satellite television, or other networked services, are detected to be online and operational, it can be inferred that the building in which these services are operational has electrical power. Conversely, if Internet of Things devices and residential services are not detected to be operational, it can be determined that a power outage is possible.

Because the absence of signals from such services may not be conclusive (i.e. those services may simply be turned off at the moment), the system may be configured to consider other information as well, to more definitively determine whether electrical power is truly unavailable. For example, emergency calling records (i.e., 911 calls), as well as other types of reporting, can be considered. If a user reported an outage, or if they reported that no lights are on in their neighbor's home, that information can be considered to piece together the conditions in the region. Other such sources of data may include vehicle communications systems. For example, many vehicles have monitoring systems to which a plurality of data is reported. If a vehicle reports an electrical short, or moisture, then it may indicate flood conditions, which could indicate a likely loss of electrical power in the region. Also, personal electronic devices, such as mobile phones, can have the battery charge state monitored remotely by the phone/data service provider. If a user's phone has a significant charge, particularly after a long duration following the occurrence of a disaster, that could indicate that they have a power source available from which they are able to charge their device.

Figure 3:
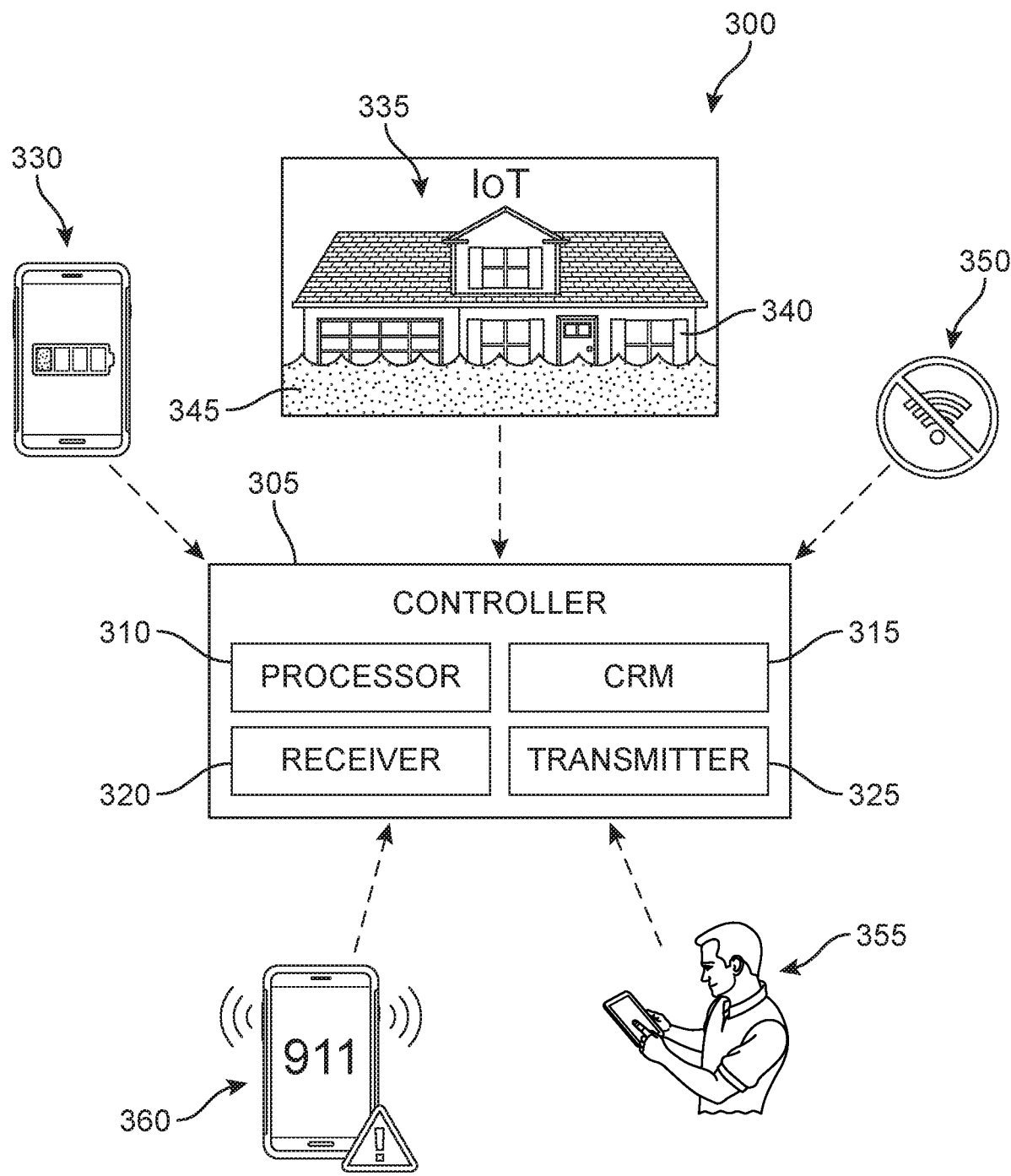
FIG. 3 is a schematic illustration of a power outage detection system.

FIG. 3 is a schematic illustration of a power outage detection system 300. FIG. 3 is a schematic network illustration of system 300. As shown in FIG. 3, system 300 may include a controller 305. Controller 305 may include various computing and communications hardware, such as servers, integrated circuits, displays, etc. Further, controller 305 may include a device processor 310 and a non-transitory computer readable medium 315 including instructions executable by device processor 310 to perform the processes discussed herein. The components of controller 305 may be implemented in association with a mobile conditions monitoring center, such as vehicle, or in association with a control center or conditions monitoring center located in a permanent building (i.e., brick and mortar establishment). Controller 305 and its components may have the same or similar features as controller 105 and its components discussed above.

Computer readable medium 315 may include instructions to perform the following steps: receiving information indicative of the status of electrical power at a plurality of locations within a geographic region; and determining the status of electrical power in the geographic region based on the status of electrical power at the plurality of locations.

As shown in FIG. 3, controller 305 may be configured to receive information regarding battery status 330 of personal electronic devices in a geographic region. If a large number of the personal electronic devices having network connections, e.g., via the Internet, are determined to have low levels of battery charge, it could be indicative that there is not any electrical power available with which to charge those devices. Accordingly, in some embodiments, the information indicative of the status of electrical power for which computer readable medium 315 includes instructions to receive includes information regarding battery state of a portable electronic device.

In addition, system 300 may receive Internet of Things information 335, as indicated in FIG. 3, by a house 340 with flood water 345. In some embodiments, the house may be equipped with one or more moisture sensors configured to detect flooding. Controller 305 may be configured to receive data from such sensors. Accordingly, in some embodiments, the information indicative of the status of electrical power for which computer readable medium 315 includes instructions to receive includes information regarding operating status of Internet of Things devices in the geographic region.

Additionally, or alternatively, in some cases, contamination of the flood water may be detected. The stippling of flood water 345 indicates contamination of flood water 345 with any of a variety of contaminants. Data indicating the presence and, in some cases magnitude, of contamination of water may be received by controller 305.

In some embodiments, the information indicative of the status of electrical power for which the computer readable medium includes instructions to receive includes information regarding usage of services that are trackable remotely. For example, information pertaining to outages of services 350, such as Internet service, electrical service, cable television service, satellite television, etc., may be received by controller 305.

In some embodiments, the information indicative of the status of electrical power for which the computer readable medium includes instructions to receive includes information regarding user reports 355 of conditions in the geographic region. For example, as shown in FIG. 3, users may submit reports of the operating status of various systems associated with their whereabouts. Such reports may be submitted in any of a variety of ways. For example, in some cases, an emergency application on the user's phone may enable the user to report on the status of one or more systems on the premises.

In some embodiments, the information indicative of the status of electrical power for which the computer readable medium includes instructions to receive includes information regarding emergency telephone calls 360 (e.g., 911 calls). Emergency call records may include reports of power outages in the caller's home or in buildings nearby.

System 300, or a third party system, may analyze the information received regarding possible power outages, and may make determinations regarding the conditions in the geographic region from which the information is received. System 300 may be configured to send information regarding the status of electrical power to inform organizations and residents of the situation. For, example, in some embodiments, computer readable medium 315 may include instructions for sending information regarding the status of electrical power to a plurality of users of system 300. For instance, users may access a website or an app on their personal electronic device to which system 300 may send reports of electrical power outages.

Another way in which the determined conditions may be communicated to others is via the preparation and distribution of a map showing the localities in which electrical power is unavailable. Accordingly, in some embodiments, computer readable medium 315 may include instructions for determining a boundary of an area in which electrical power is unavailable, and preparing a map that illustrates the boundary.

Figure 4:
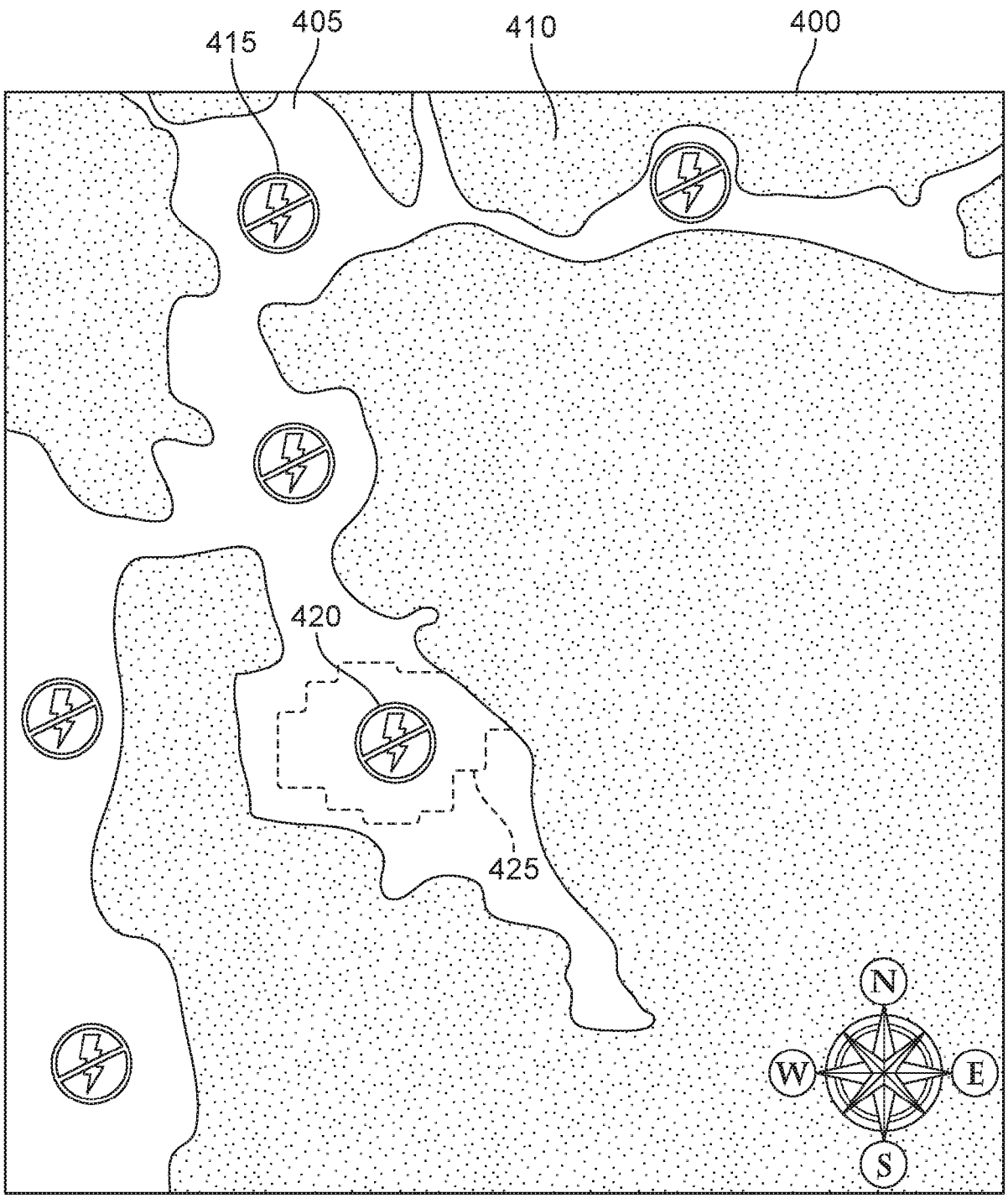
FIG. 4 is a schematic illustration of a map showing locations of power outages.

FIG. 4 is a schematic illustration of a map showing locations of power outages. FIG. 4 shows a map 400, illustrating land areas 405 and water areas 410. Map 400 shows areas with power outages using a power outage symbol 415, which may illustrate general areas in which electrical power is unavailable. In some cases, map 400 may illustrate boundaries defining the areas in which electrical power is available and unavailable. For example, in another area, a second power outage symbol 415 labels an area defined by a boundary 425, which identifies the boundary between the area of the power outage inside boundary 425 and the area where electrical power is available (i.e., outside boundary 425.

Affirmative data and reports regarding the availability of power are beneficial to determining power outage conditions in a given geographic area. Data and reports that positively indicate the availability of power are definitive, whereas the data and reports indicative of the absence of power can be inconclusive. In some embodiments, computer readable medium 415 may include instructions for determining that a user within the geographic region has electrical power available based the information received, and preparing a map that indicates that an area proximate to the user in the geographic region has electrical power available. Accordingly, preparing the map include determining a boundary of an area in which electrical power is available.

Other sources of information indicative of power outages may include information regarding operating status of onboard automobile diagnostics. Vehicle diagnostics monitoring and reporting systems may indicate electrical shorts and/or a complete lack of signal, either of which may indicate a possible flood. If the flood has damaged the electrical system of the vehicle, it may also render electrical power unavailable in local building structures.

Figure 5:
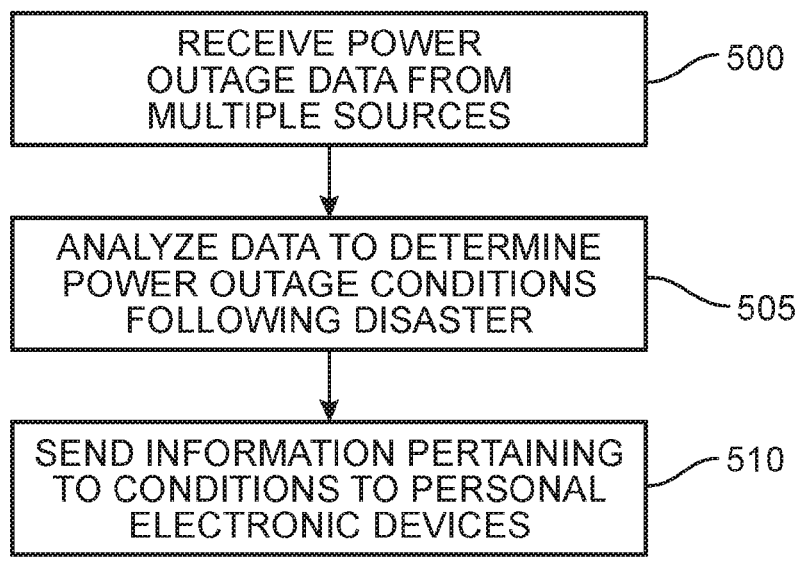
FIG. 5 is a flowchart illustrating a process of analyzing and utilizing power outage data.

FIG. 5 is a flowchart illustrating a process of analyzing and utilizing power outage data. As shown in FIG. 5, the computer readable medium may include instructions for receiving power outage data from multiple sources (step 500). In addition, the computer readable medium may include instructions for analyzing the data to determine power outage conditions, e.g., following a disaster (step 505). Further, the computer readable medium may include instructions for sending information pertaining to power outage conditions to personal electronic devices of users who may have an interest in the information (step 510).

The broadcast of information may be sent to any suitable groups of persons. For example, in some cases, the information may be sent to users of the system. For example, users may register for access to the information broadcast by the system. Such broadcasts may be sent via email, text message, or simply made available via a website or an application for a personal electronic device. Such information could also be made available to the general public, via a webpage. In some cases, the broadcasts may be targeted to cellular users in a geographic region, whether they are registered with the system or not. For example, warnings or alerts may be sent to the users for all cellular carriers in the region.

Figure 6:
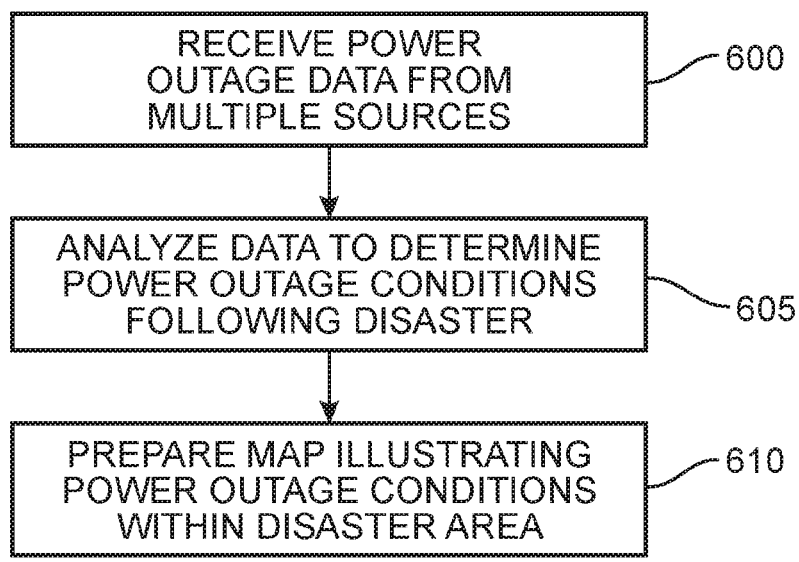
FIG. 6 is a flowchart illustrating another process of analyzing and utilizing power outage data.

FIG. 6 is a flowchart illustrating another process of analyzing and utilizing power outage data. As shown in FIG. 6, the computer readable medium may include instructions for receiving power outage data from multiple sources (step 600). In addition, the computer readable medium may include instructions for analyzing the data to determine power outage conditions, e.g., following a disaster (step 605). Further, the computer readable medium may include instructions for preparing a map illustrating power outage conditions within a geographic region, such as a disaster area (step 610).

Water Contamination

A monitoring system can be used to detect whether contaminants, such as organic pollutants, such as sewage or biohazardous waste; chemical pollutants, such as petroleum based compounds (e.g., oil, gasoline, etc.), coal ash, and other chemical compositions; or other dangerous or otherwise undesirable items, are found in water. Alternatively, or additionally, the monitoring system may be configured to detect whether animals, such as snakes or insects (e.g., fire ants), are found in water. Contamination may be monitored in flood waters and/or pre-existing bodies of water (i.e., bodies of water that existed prior to a disaster occurred). In some cases, contamination sensors that are disposable may be used. Such sensors can feed back information and ultimately wash away out of range and/or run out of battery. This can be done for fires or other disasters as well.

Figure 7:
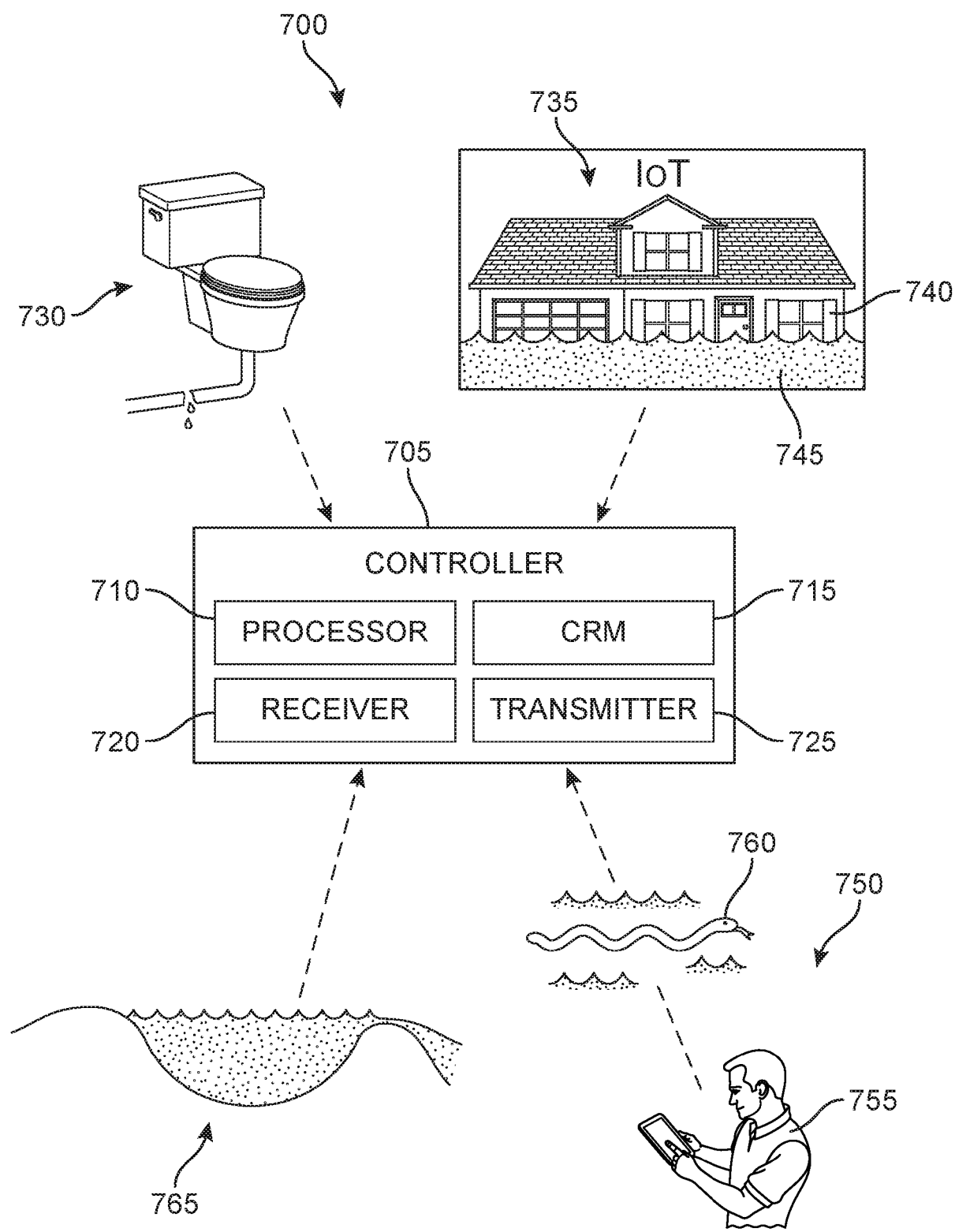
FIG. 7 is a schematic illustration of a water contamination monitoring system.

FIG. 7 is a schematic illustration of a water contamination monitoring system. FIG. 7 is a schematic network illustration of system 700. As shown in FIG. 7, system 700 may include a controller 705. Controller 705 may include various computing and communications hardware, such as servers, integrated circuits, displays, etc. Further, controller 705 may include a device processor 710 and a non-transitory computer readable medium 715 including instructions executable by device processor 710 to perform the processes discussed herein. The components of controller 705 may be implemented in association with a mobile conditions monitoring center, such as vehicle, or in association with a control center or conditions monitoring center located in a permanent building (i.e., brick and mortar establishment). Controller 705 and its components may have the same or similar features as controller 105 and its components discussed above.

Computer readable medium 715 may include instructions to perform the following steps: receiving information indicative of the presence of one or more contaminants in water within a geographic region; and determining a characterization of water contamination within the geographic region.

As shown in FIG. 7, controller 705 may be configured to receive information regarding sewage contamination 730 in a geographic region. Such information can be collected by various sewage sensors that may be deployed in flood waters or pre-existing bodies of water.

In addition, system 700 may receive Internet of Things information 735, as indicated in FIG. 7, by a house 740 with flood water 745. In some embodiments, the house may be equipped with one or more moisture sensors configured to detect flooding. Also, as indicated by stippling in flood water 745, contamination may also be detected in flood water 745. Further, Internet of Things sensors may also be configured to detect contamination in the water supply of a home or building. Controller 705 may be configured to receive data from such sensors.

In some embodiments, the information indicative of water contamination may be sent to one or more parties. For example, computer readable medium 715 may include instructions for sending information regarding water contamination to a plurality of users of system 700.

When flooding occurs, the presence of various types of dangerous animals in the flood waters can be a concern. Accordingly, in some embodiments, computer readable medium 715 may include instructions for receiving information 750 regarding the presence of one or more predetermined types of animals in water. Such information may be received in the form of reports from system users, 911 callers, or other reporting platforms. For example, as shown in FIG. 7, a user 755 may report the presence of dangerous animals, such as snakes 760 in flood waters or in pre-existing bodies of water in which such animals are not typically found, or are not typically found in as high of a population.

Flooded coal ash ponds can contaminate not only flood waters, but also pre-existing bodies of water and local water supplies. Accordingly, computer readable medium 715 may also include instructions for receiving information regarding coal ash content 765, illustrated in FIG. 7 by an overflowing coal ash pond.

In some embodiments, system 700 may be configured to send information regarding the water contamination to inform organizations and residents of the situation. For, example, in some embodiments, computer readable medium 715 may include instructions for sending information regarding water contamination to a plurality of users of system 700. For instance, users may access a website or an app on their personal electronic device to which system 700 may send reports of electrical power outages.

Another way in which the determined conditions may be communicated to others is via the preparation and distribution of a map showing the localities in which water contamination has been detected. Accordingly, in some embodiments, computer readable medium 715 may include instructions for preparing a map indicating the location of contamination in the water in the geographic region.

Figure 8:
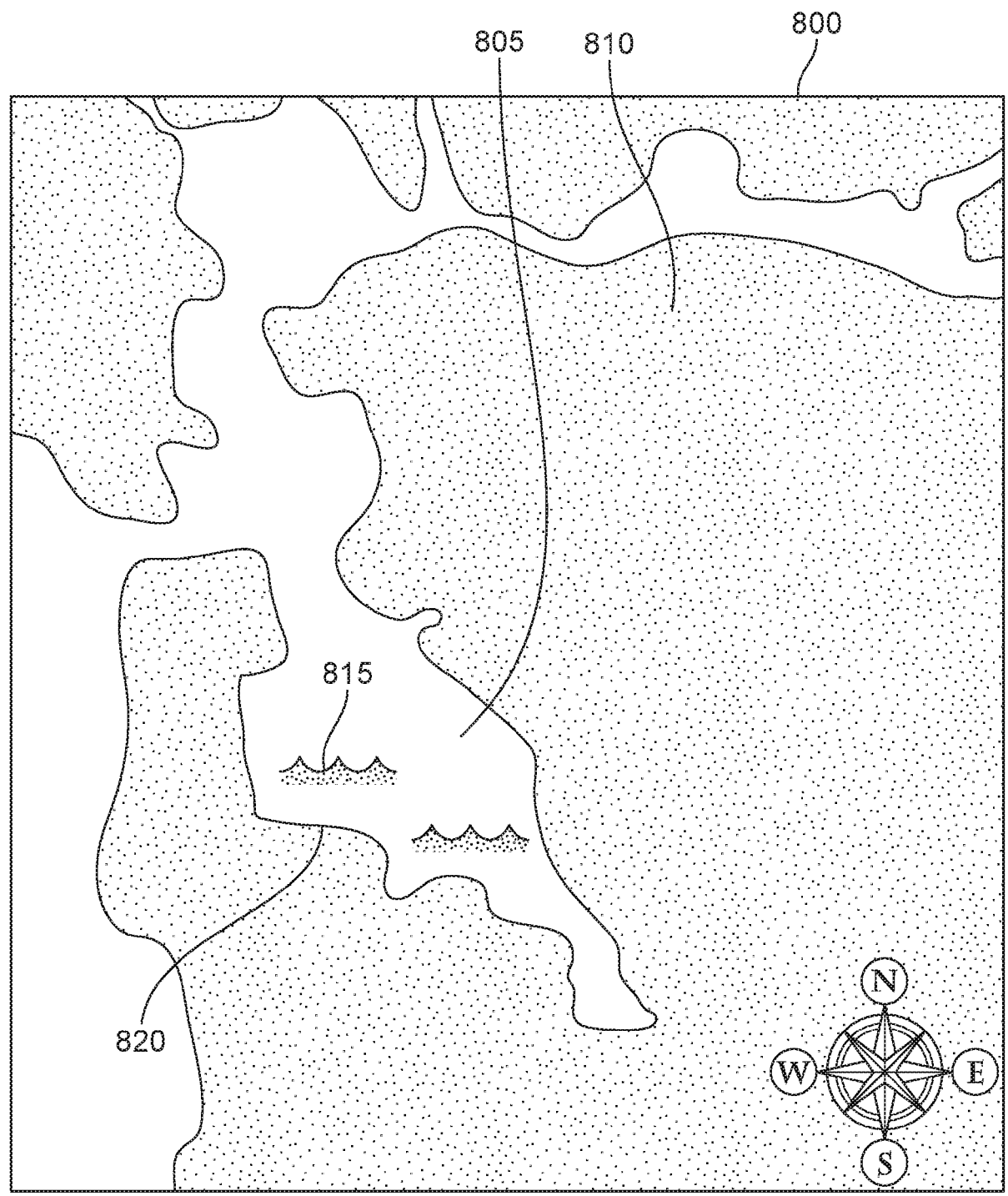
FIG. 8 is a schematic illustration of a map showing locations of contaminated flood waters.

FIG. 8 is a schematic illustration of a map showing locations of contaminated flood waters. FIG. 8 shows a map 800, illustrating land areas 805 and water areas 810. Map 800 shows areas with flood water contamination using a water contamination symbol 815, which may illustrate general areas in which electrical power is unavailable. As shown in FIG. 8, the flood waters may be found along a coastline 820 of water 810.

Figure 9:
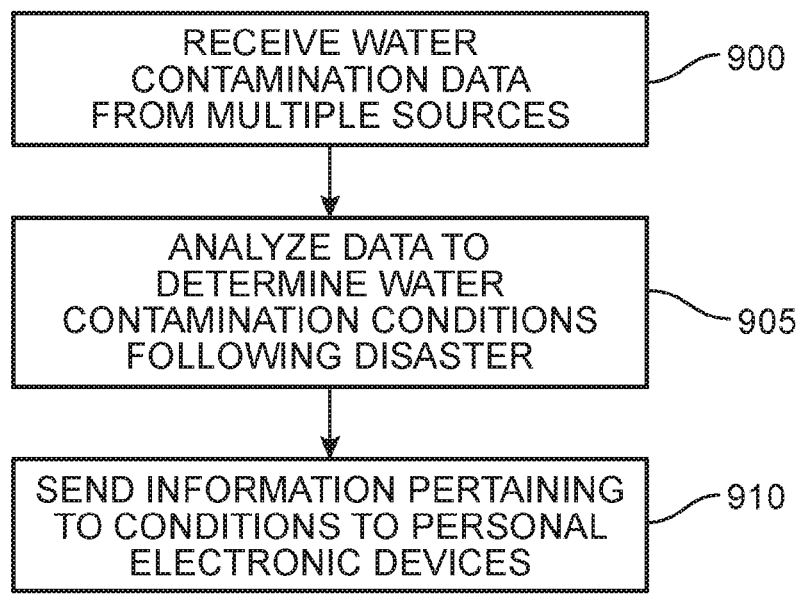
FIG. 9 is a flowchart illustrating a process of analyzing and utilizing water contamination data.

FIG. 9 is a flowchart illustrating a process of analyzing and utilizing water contamination data. As shown in FIG. 9, the computer readable medium may include instructions for receiving information indicative of the presence of one or more contaminants in a body of water within a geographic region from multiple sources (step 900). In addition, the computer readable medium may include instructions for analyzing the data to determine water contamination conditions, e.g., following a disaster (step 905). Further, the computer readable medium may include instructions for sending information pertaining to water contamination conditions to personal electronic devices of users who may have an interest in the information (step 910).

Figure 10:
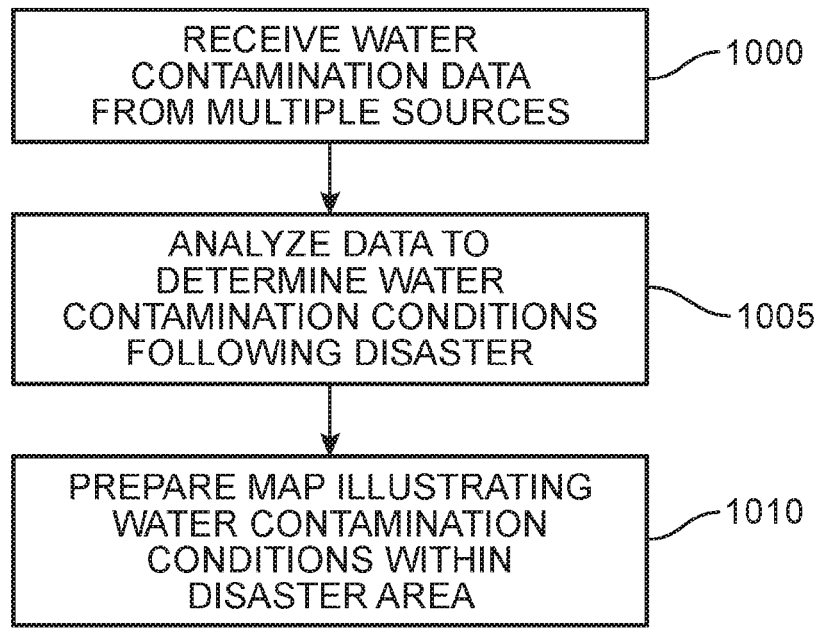
FIG. 10 is a flowchart illustrating another process of analyzing and utilizing water contamination data.

FIG. 10 is a flowchart illustrating another process of analyzing and utilizing water contamination data. As shown in FIG. 10, the computer readable medium may include instructions for receiving information indicative of the presence of one or more contaminants in a body of water within a geographic region from multiple sources (step 1000). In addition, the computer readable medium may include instructions for analyzing the data to determine water contamination conditions, e.g., following a disaster (step 1005). Further, the computer readable medium may include instructions for preparing a map indicating the location of contamination in the water in the geographic region (step 1010).

Figure 11:
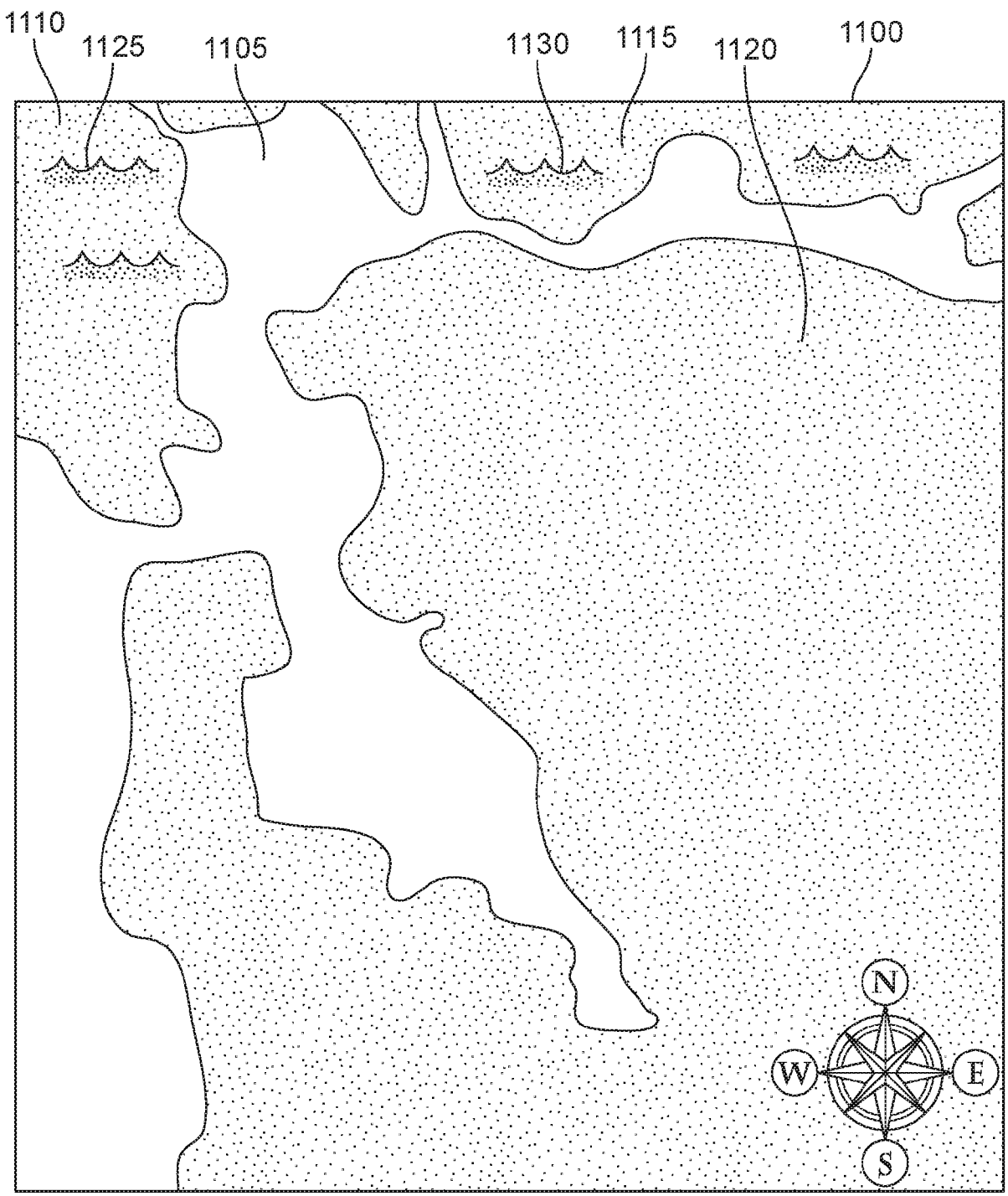
FIG. 11 is a schematic illustration of a map showing locations of contaminated bodies of water.

As noted above, contamination may be detected in drinking water, flood water, and/or pre-existing bodies of water. FIG. 11 is a schematic illustration of a map showing locations of contaminated bodies of water. FIG. 11 shows a map 1100, illustrating land areas 1105 and bodies of water, such as a first body of water 1110, a second body of water 1115, and a third body of water 1120. These bodies of water may be pre-existing or may be formed by flood waters. Map 1100 shows areas with flood water contamination. For example, a first stippled water contamination symbol 1125 indicates contamination in first body of water 1110. A second stippled water contamination symbol 1130 indicates water contamination in second body of water 1115.

Pre-existing Networks

Information from various pre-existing networks may be utilized to determine the status of geographic regions following a disaster. For example, networks such as traffic lights, utilities info, road closures, service providers (cable, internet, etc.), and other sources can be considered. Also, information from Internet of Things sensors can be reviewed. This information can be used to determine disaster response strategies. Information from vehicle diagnostics and reporting systems can also be used. For example, glass breakage detectors, car alarms, or even a lack of reporting from a vehicle can indicate a noteworthy status.

Figure 12:
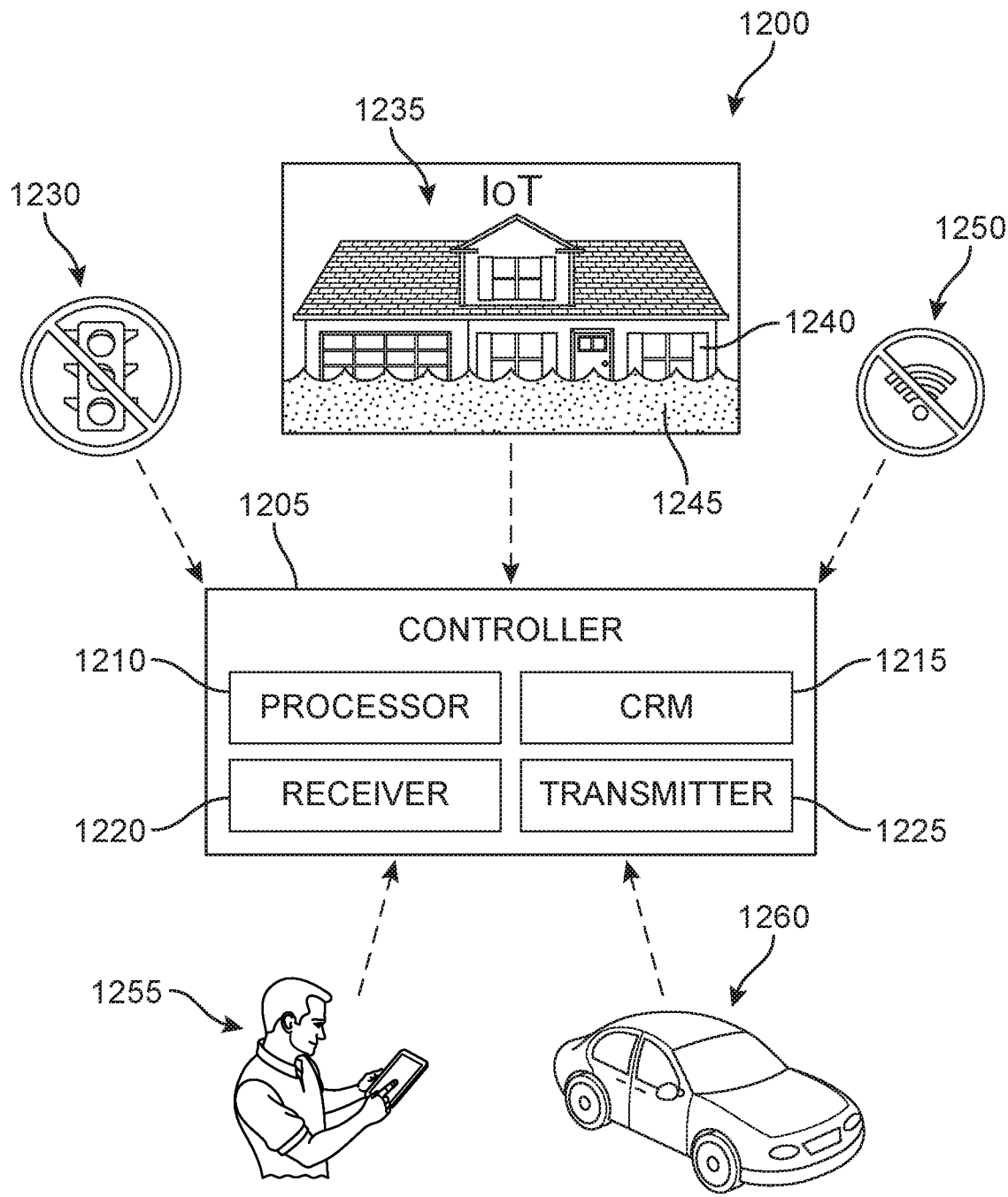
FIG. 12 is a schematic illustration of a post-disaster monitoring system configured to receive data from multiple pre-existing networks.

FIG. 12 is a schematic illustration of a post-disaster monitoring system configured to receive data from multiple pre-existing networks. FIG. 12 is a schematic network illustration of system 1200. As shown in FIG. 12, system 1200 may include a controller 1205. Controller 1205 may include various computing and communications hardware, such as servers, integrated circuits, displays, etc. Further, controller 1205 may include a device processor 1210 and a non-transitory computer readable medium 1215 including instructions executable by device processor 1210 to perform the processes discussed herein. The components of controller 1205 may be implemented in association with a mobile conditions monitoring center, such as vehicle, or in association with a control center or conditions monitoring center located in a permanent building (i.e., brick and mortar establishment). Controller 1205 and its components may have the same or similar features as controller 105 and its components discussed above.

Computer readable medium 1215 may include instructions to perform the following steps: receiving information from one or more pre-existing networks; and determining conditions in a geographic region based on the information received from the one or more pre-existing networks.

As shown in FIG. 12, among the pre-existing networks from which computer readable medium 1215 has instructions to receive information is a traffic lights network 1230. Information from the traffic lights network regarding operation, outages, etc. of the traffic lights in a geographic region may enable determinations regarding various conditions in the region, such as electrical power outages, traffic irregularities, and other conditions. Similarly, system 1200 may also be configured to receive information regarding road closures.

In addition, system 1200 may receive Internet of Things information 1235, as indicated in FIG. 12, by a house 1240 with flood water 1245. In some embodiments, the house may be equipped with one or more moisture sensors configured to detect flooding. Also, as indicated by stippling in flood water 1245, contamination may also be detected in flood water 1245. Also, in some embodiments, air quality sensors may be networked via an Internet of Things system. Controller 705 may be configured to receive data from various sensors such as those mentioned above. Controller 705 may be configured to receive data from such sensors. Further, many other types of Internet of Things data can be collected by various devices connected to the Internet of Things. In addition, system 1200 may be configured to receive information from Internet of Things devices in multiple buildings in a geographic region. Operational status, power supply status, and other measurements and reporting from networked Internet of Things devices and sensors can provide a great deal of information from which post-disaster conditions may be assessed.

In some embodiments, among the information from pre-existing networks which computer readable medium 1215 has instructions to receive is service provider information 1250 from residential service provider networks. Such networks may be associated with various monitored services provided to homes and businesses, such as cable television, satellite television, Internet service, and other such services. Similarly, the pre-existing networks from which system 1200 may receive information may include public utilities networks.

In some embodiments, among the information from pre-existing networks which computer readable medium 1215 has instructions to receive is vehicle information 1260 from vehicle diagnostics and reporting systems. Information such as poor electrical system health may indicate flooding. Information such as vehicle alarm tripping and/or glass breakage may indicate hail damage. Additionally, some information may be collectively analyzed across multiple vehicles to make determinations of general conditions within a geographic region. For example, in the days following a disaster, if a majority of vehicles in the region have low fuel levels, this may indicate a lack of availability of fuel in the area. The same may be true for electrical vehicles with respect to charging.

In some embodiments, system 1200 may be configured to send information regarding the determined conditions to inform organizations and residents of the situation. For, example, in some embodiments, computer readable medium 1215 may include instructions for sending information regarding water contamination to a plurality of users of system 1200. For instance, users may access a website or an app on their personal electronic device to which system 1200 may send reports of electrical power outages.

Another way in which the determined conditions may be communicated to others is via the preparation and distribution of a map showing the conditions in the area. Accordingly, in some embodiments, computer readable medium 1215 may include instructions for preparing a map indicating the conditions within the geographic region.

Figure 13:
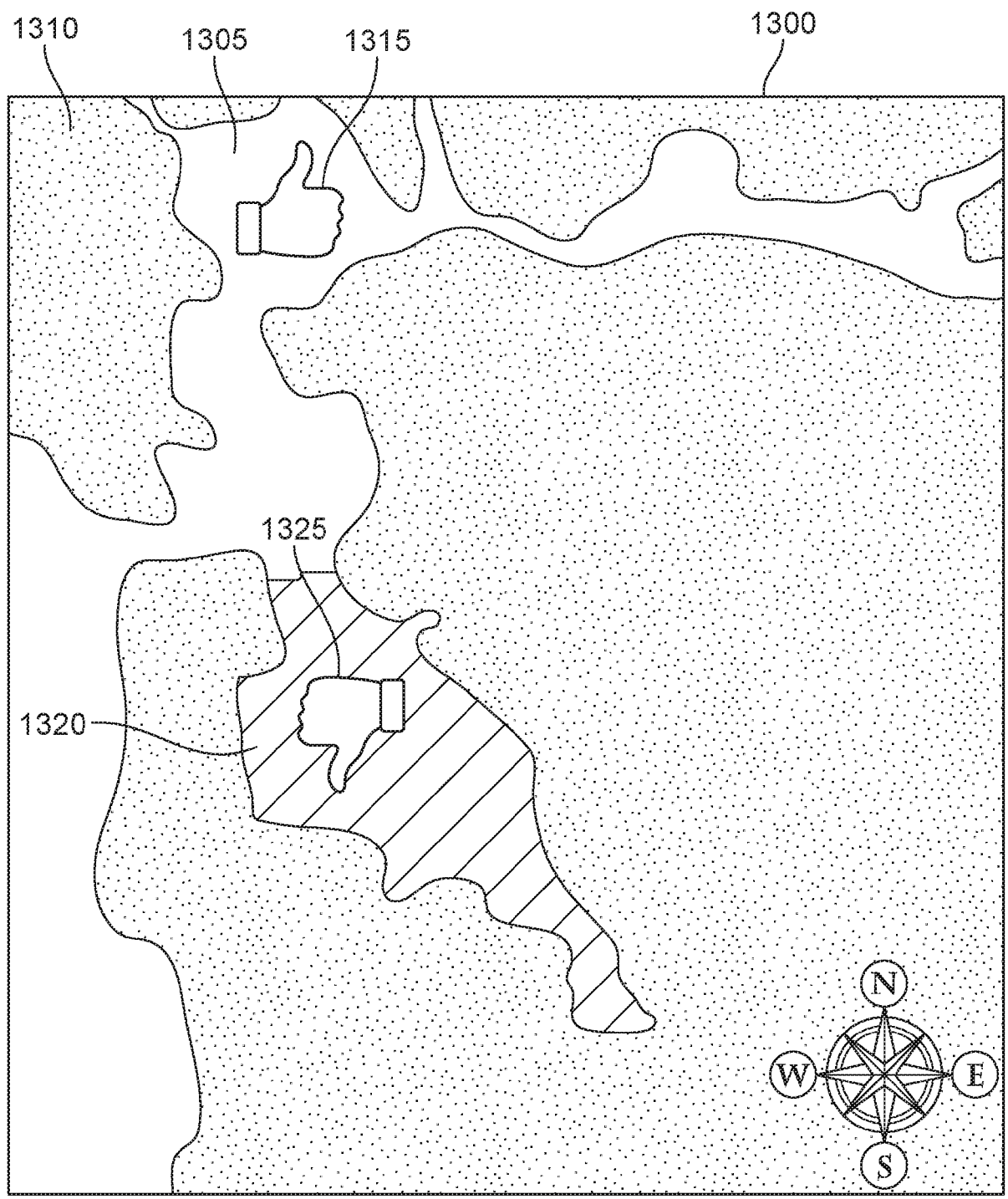
FIG. 13 is a schematic illustration of a map showing locations where conditions are favorable and unfavorable based on the data obtained from pre-existing networks.

FIG. 13 is a schematic illustration of a map showing locations of contaminated flood waters. FIG. 13 illustrates a map 1300, showing the general status of conditions in localities within a geographic region. For example, map 1300 illustrates land areas 1305 and water areas 1310. Map 1300 shows areas with a generally good post-disaster condition with a thumbs-up symbol 1315. Conversely, map 1300 shows an area 1320 having generally poor post-disaster conditions with a thumbs-down symbol 1325. It will be noted that these schemes and symbols are intended to be purely schematic and that any suitable symbols or conventions may be used for map 1300.

Figure 14:
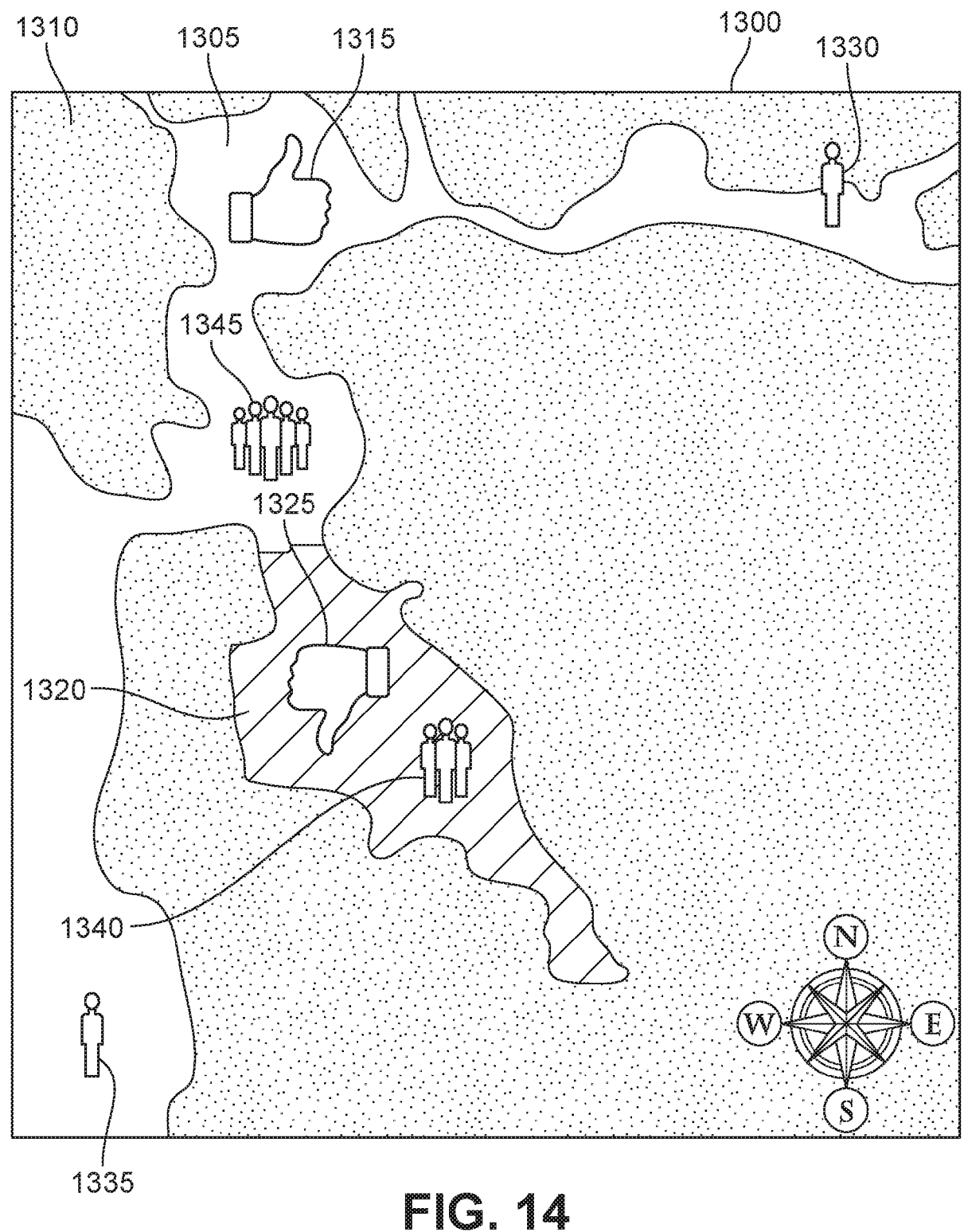
FIG. 14 is a schematic illustration of the map of FIG. 13 with an additional layer of population density data added.

In some embodiments, the map may include multiple layers of information regarding post-disaster conditions, with each layer providing more detailed information regarding various conditions. FIG. 14 shows map 1300 with additional information incorporated. For instance, map 1300 may include population density information. As shown in FIG. 14, a first symbol 1330 and a second symbol 1335 indicate areas with a relatively low population density. A third symbol 1340 indicates an area with a higher population density. And a fourth symbol 1345 indicates an area with the highest population density. Knowing about population density in conjunction with general or specific conditions can assist disaster responders in prioritizing the areas that can help the most people in the shortest amount of time. For example, if two areas both have poor conditions, but one area is more densely populated, responders can focus their initial efforts on the more populated area in order to help the most people as soon as possible. More specifically, with more detailed conditions information, decisions can be made depending on which type of conditions the residents are under. For example, if one area has no electrical power, and a second area is inundated with contaminated flood waters, relief efforts may choose to assist those in the flood area as a priority. However, if the flooded area is mostly unpopulated, efforts may be better spent on assisting those in the power outage area.

Figure 15:
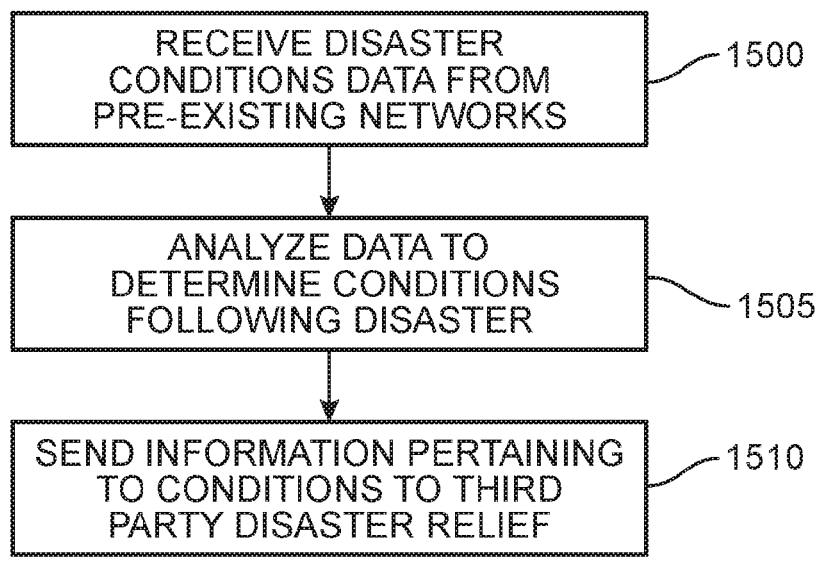
FIG. 15 is a flowchart illustrating a process of analyzing and utilizing data from pre-existing networks.

FIG. 15 is a flowchart illustrating a process of analyzing and utilizing data received from pre-existing networks. As shown in FIG. 15, the computer readable medium may include instructions for receiving information from multiple pre-existing network sources (step 1500). In addition, the computer readable medium may include instructions for analyzing the data to determine disaster conditions (step 1505). Further, the computer readable medium may include instructions for sending information pertaining to the determined conditions to persons or organizations who may have an interest in the information. For example, the system may be configured to send the information to a third party associated with disaster response (step 1510). Alternatively, or additionally, the system may be configured to send the information to personal electronic devices of users of the system.

Figure 16:
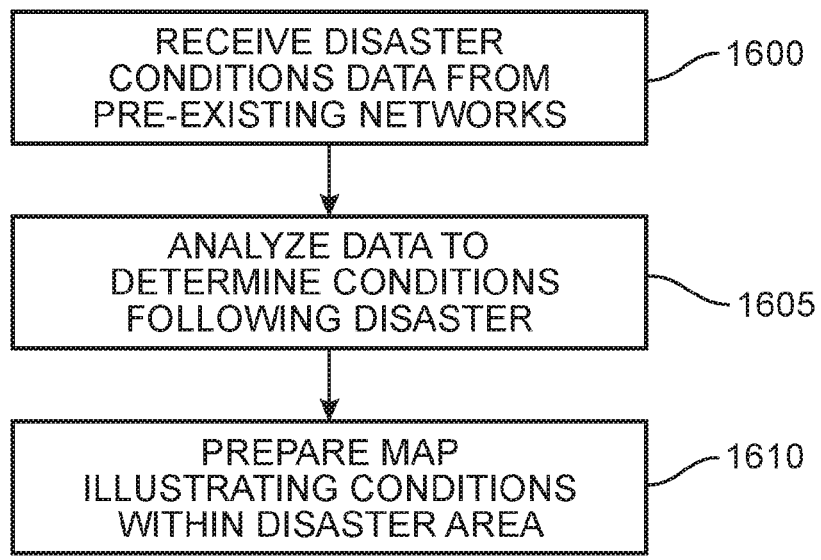
FIG. 16 is a flowchart illustrating another process of analyzing and utilizing data from pre-existing networks.

FIG. 16 is a flowchart illustrating another process of analyzing and utilizing data received from pre-existing networks. As shown in FIG. 16, the computer readable medium may include instructions for receiving information from multiple pre-existing network sources (step 1600). In addition, the computer readable medium may include instructions for analyzing the data to determine disaster conditions (step 1605). Further, the computer readable medium may include instructions for preparing a map illustrating the detected conditions in the geographic region (step 1610). The map may include multiple layers of information regarding the determined conditions.

Figure 17:
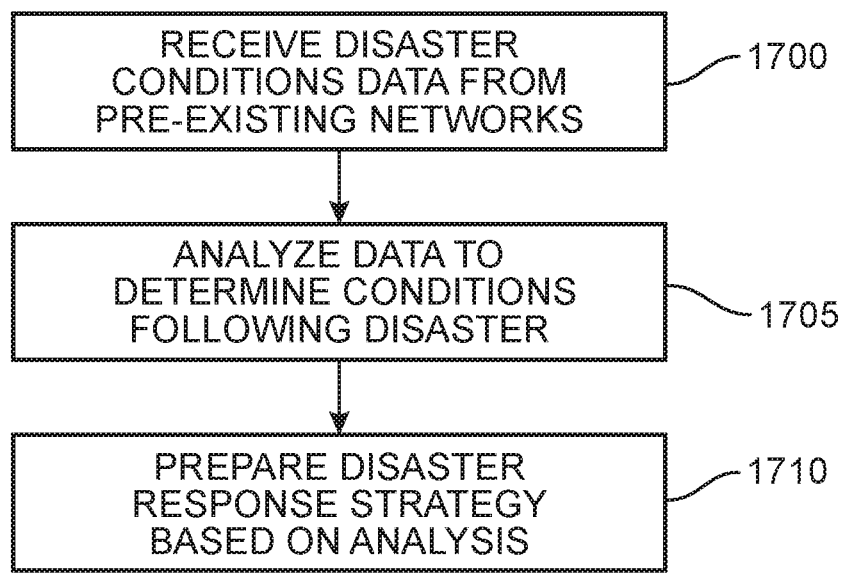
FIG. 17 is a flowchart illustrating another process of analyzing and utilizing data from pre-existing networks.

FIG. 17 is a flowchart illustrating another process of analyzing and utilizing data received from pre-existing networks. As shown in FIG. 17, the computer readable medium may include instructions for receiving information from multiple pre-existing network sources (step 1700). In addition, the computer readable medium may include instructions for analyzing the data to determine disaster conditions (step 1705). Further, the computer readable medium may include instructions for preparing disaster response strategies based on the analysis (step 1710).

Crowd Source Imagery

Crowd source imagery can be collected to determine information about post-disaster conditions in a geographic area. Information can be collected from personal electronic devices, such as mobile phones and other devices. In some embodiments, a platform may be provided for users to upload their images.

Figure 18:
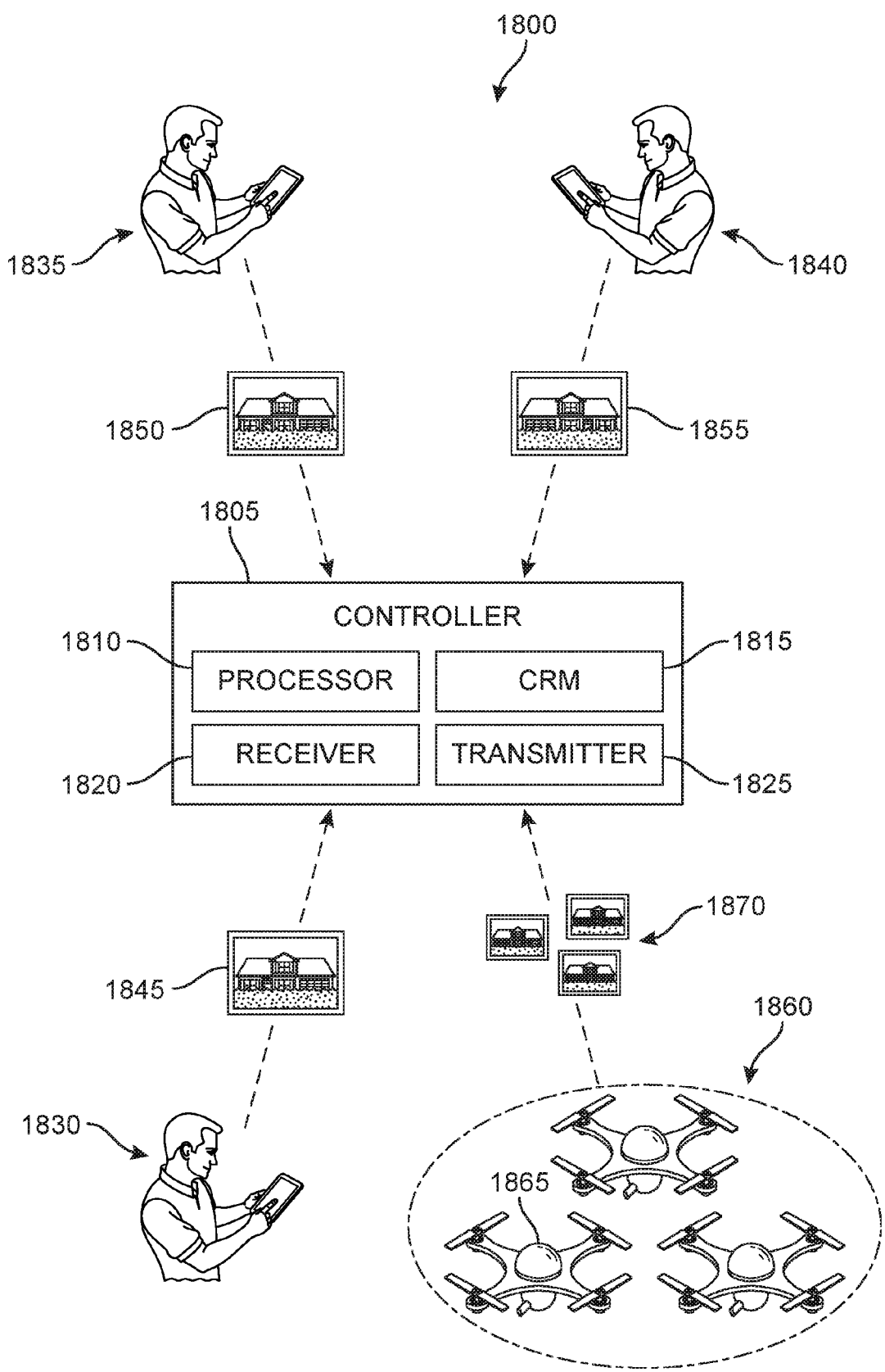
FIG. 18 is a schematic illustration of a post-disaster monitoring system configured to receive crowd sourced images.

FIG. 18 is a schematic illustration of a post-disaster monitoring system configured to receive data from multiple pre-existing networks. FIG. 18 is a schematic network illustration of system 1800. As shown in FIG. 18, system 1800 may include a controller 1805. Controller 1805 may include various computing and communications hardware, such as servers, integrated circuits, displays, etc. Further, controller 1805 may include a device processor 1810 and a non-transitory computer readable medium 1815 including instructions executable by device processor 1810 to perform the processes discussed herein. The components of controller 1805 may be implemented in association with a mobile conditions monitoring center, such as vehicle, or in association with a control center or conditions monitoring center located in a permanent building (i.e., brick and mortar establishment). Controller 1805 and its components may have the same or similar features as controller 105 and its components discussed above.

Computer readable medium 1815 may include instructions to perform the following steps: receiving a plurality of images from a plurality of personal devices in a geographic region; and determining conditions in a geographic region based on the information received from the plurality of images. In some embodiments, the personal devices may include personal electronic devices, such as smart phones or tablet computers. In some embodiments, the personal devices may include other types of devices, such as drones with photographic capability.

As shown in FIG. 18, system 1800 may be configured to receive photographic images from a plurality of personal electronic devices. Generally, the more devices and photos are received, the more accurate determinations of post-disaster conditions may be. For purposes of illustration and clarity, FIG. 18 shows only three users, including a first user 1830, a second user 1835, and a third user 1840. As shown in FIG. 18, controller 1805 may be configured to receive photographic images from first user's personal electronic device, as indicated by a first photo 1845. Further, controller 1805 may be configured to receive photographic images from second user's personal electronic device, as indicated by a second photo 1850. In addition, controller 1805 may be configured to receive photographic images from third user's personal electronic device, as indicated by a third photo 1855.

As also shown in FIG. 18, photos 1870 may be received from a fleet 1860 of drones 1865. In some embodiments, one or more drones of drone fleet 1870 may be part of system 1800. In some embodiments, one or more of the drones in drone fleet 1870 may be personal drones owned and/or operated by a user who is otherwise unaffiliated with system 1800.

In some embodiments, the images may be delivered directly from the drones to controller 1805. In such embodiments, the drones may include equipment configured to complete such transmission of image files to a remote location, such as controller 1805. In some embodiments, the images may be delivered through an intermediate device, such as the drone user's smart phone or personal computer. The images may then be delivered from the smart phone or personal computer. In some cases, one or more drones of fleet 1860 may be brought back to the condition monitoring center to be plugged directly into controller 1805 for download of the images stored on board the drone.

In some embodiments, the photos from personal electronic devices and/or from drones may be received with time and/or location information embedded with the image file. This may facilitate the analysis of the imagery in order to determine the collective implication with respect to post-disaster conditions in the geographic area from which the images are collected.

Various post-disaster conditions may be detectable via the analysis of crowd sourced imagery. For example, in some embodiments, computer readable medium 1815 may include instructions for detecting flooding from the plurality of images. In some embodiments, computer readable medium 1815 may include instructions for detecting wind damage from the plurality of images. In some embodiments, computer readable medium 1815 may include instructions for detecting hail damage from the plurality of images. In some embodiments, computer readable medium 1815 may include instructions for detecting electrical power outages from the plurality of images.

In some embodiments, system 1800 may be configured to send information regarding the determined conditions to inform organizations and residents of the situation. Another way in which the determined conditions may be communicated to others is via the preparation and distribution of a map showing the conditions in the area. Accordingly, in some embodiments, computer readable medium 1815 may include instructions for preparing a map indicating the conditions within the geographic region.

Figure 19:
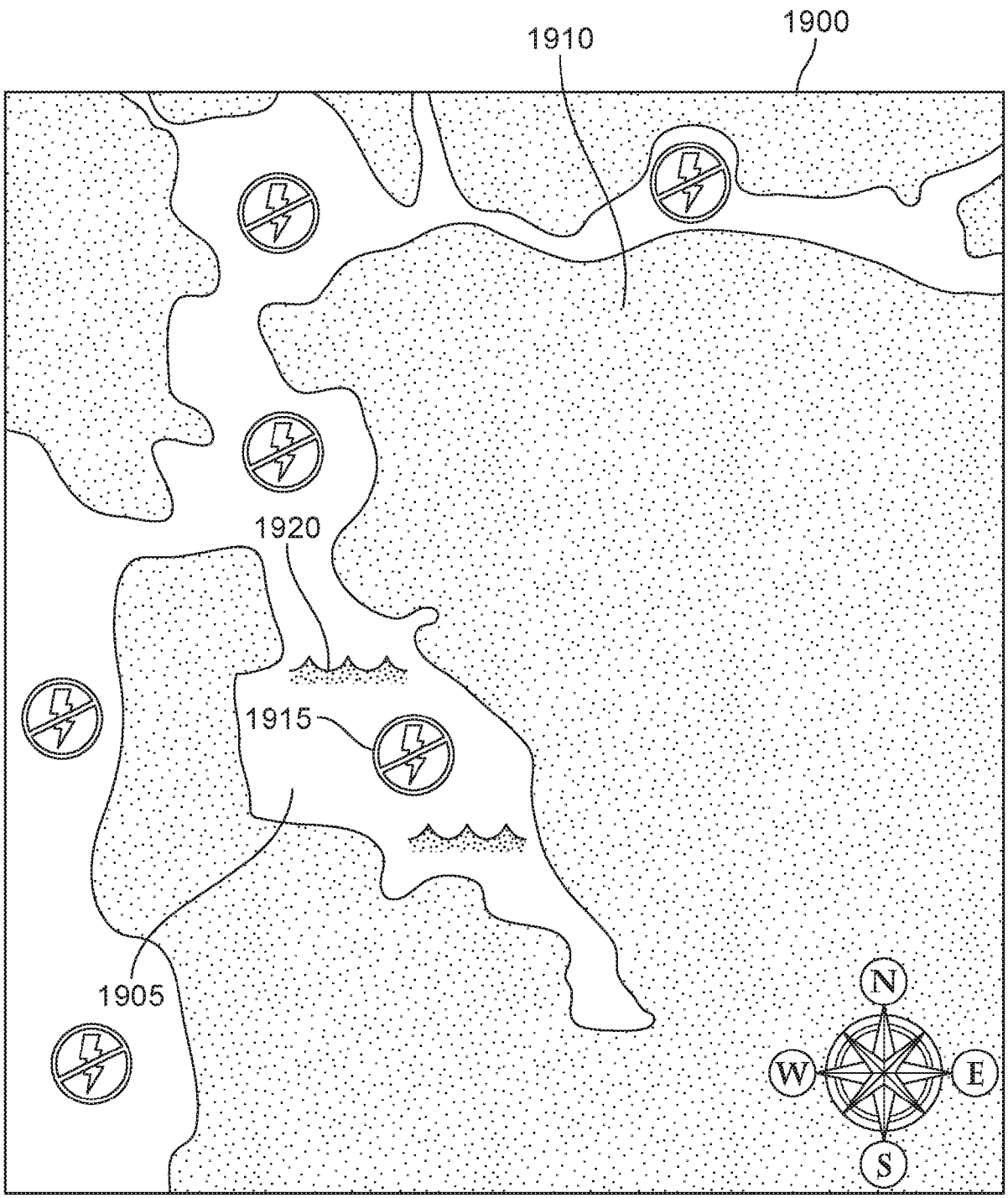
FIG. 19 is a schematic illustration of a map showing locations of power outages and contaminated flood waters.

FIG. 19 is a schematic illustration of a map showing locations of power outages and contaminated flood waters. FIG. 19 illustrates a map 1900, showing the general status of conditions in localities within a geographic region. For example, map 1900 illustrates land areas 1905 and water areas 1910. Map 1900 also includes a first symbol 1915 indicating areas where electrical power is unavailable.

Map 1900 may include multiple layers of information regarding various post-disaster conditions. For example, in addition to indicating the locations of power outages, map 1900 may include a second symbol 1920 indicating the locations of flood waters. Other layers of information may also be included on map 1900. For example, in some embodiments, map 1900 may include information regarding population density in the geographic region. These layers may be selected and deselected in order to customize the display of map 1900 to show the information desired by the user.

In some embodiments, the system may be configured to determine the areas of a given geographic region for which images are still needed in order to assess the conditions in those areas. Users of the system may be able to volunteer their services in obtaining photographic images in one or more areas identified by the system as being in need of images.

Figure 20:
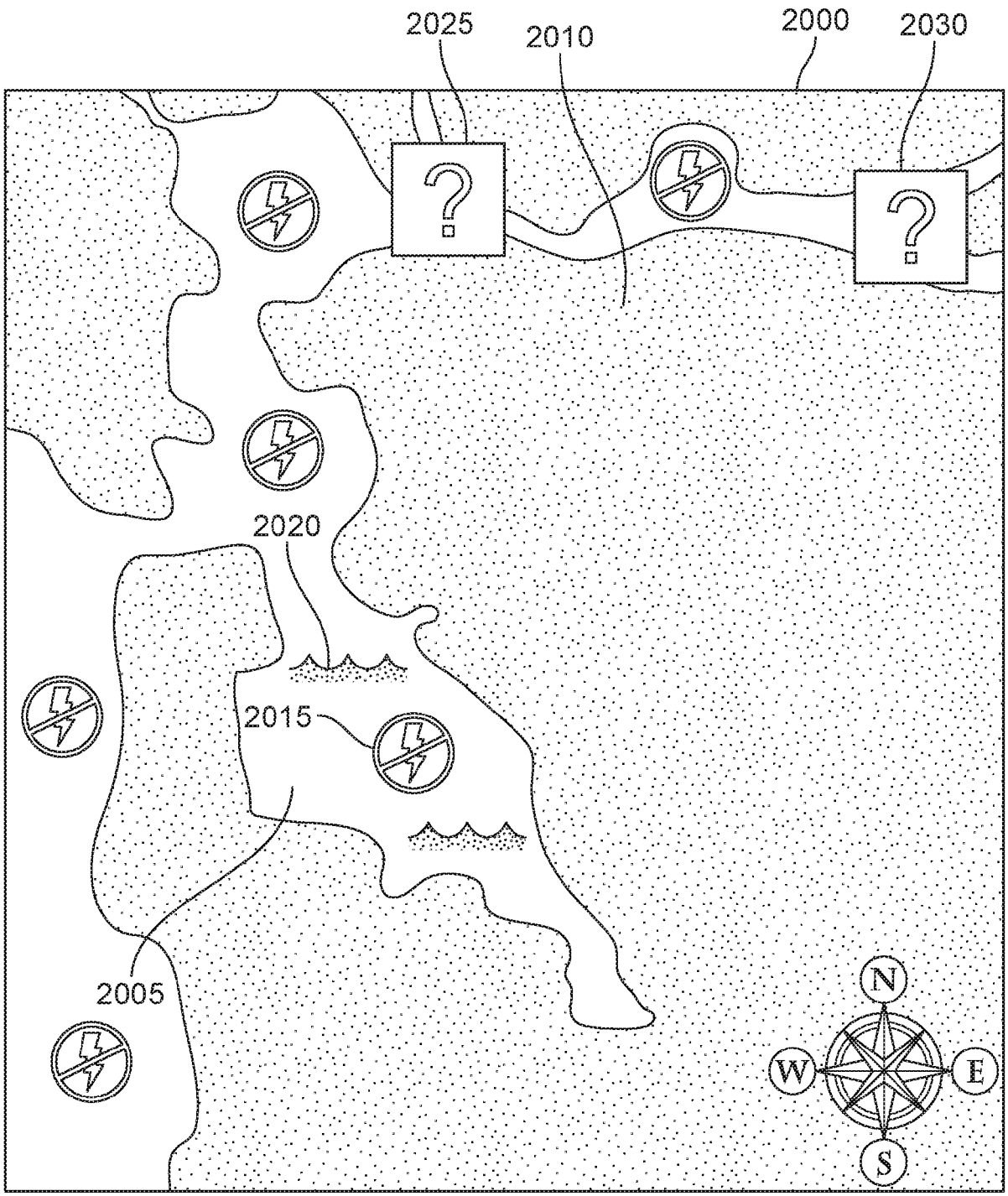
FIG. 20 is a schematic illustration of a map showing locations where additional images are needed to complete the map.

In some embodiments, the system may produce a map, viewable by users of the system, that indicates the areas from with imagery is needed. FIG. 20 is a schematic illustration of a map showing locations where additional images are needed to complete the map. Map 2000 illustrates land areas 2005 and water areas 2010. Map 2000 also includes a first symbol 2015 indicating areas where electrical power is unavailable, and a second symbol 2020 indicating areas of flooding. In addition, FIG. 20 shows a first blank area 2025 and a second blank area 2030, indicating areas from which imagery is needed. A map such as map 2000 may provide guidance to users by ensuring that their volunteer assistance with photography produces the most useful information rather than simply duplicating information that has already been obtained.

Figure 21:
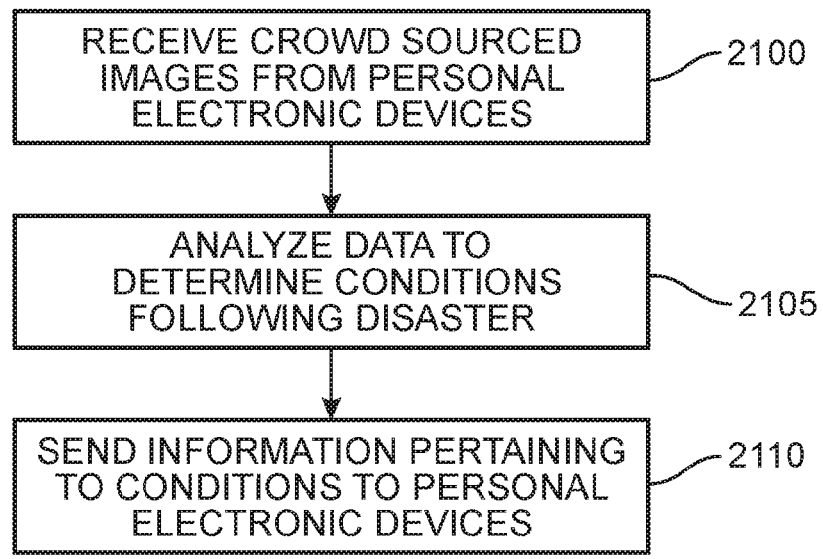
FIG. 21 is a flowchart illustrating a process of analyzing and utilizing crowd sourced images.

FIG. 21 is a flowchart illustrating a process of analyzing and utilizing crowd sourced images. As shown in FIG. 21, the computer readable medium may include instructions for receiving crowd sourced images from personal electronic devices (step 2100). In addition, the computer readable medium may include instructions for analyzing the data to determine disaster conditions (step 2105). Further, the computer readable medium may include instructions for sending information pertaining to the determined conditions to persons or organizations who may have an interest in the information. For example, the system may be configured to send the information to a third party associated with disaster response. Alternatively, or additionally, the system may be configured to send the information to personal electronic devices of users of the system (step 2110).

Figure 22:
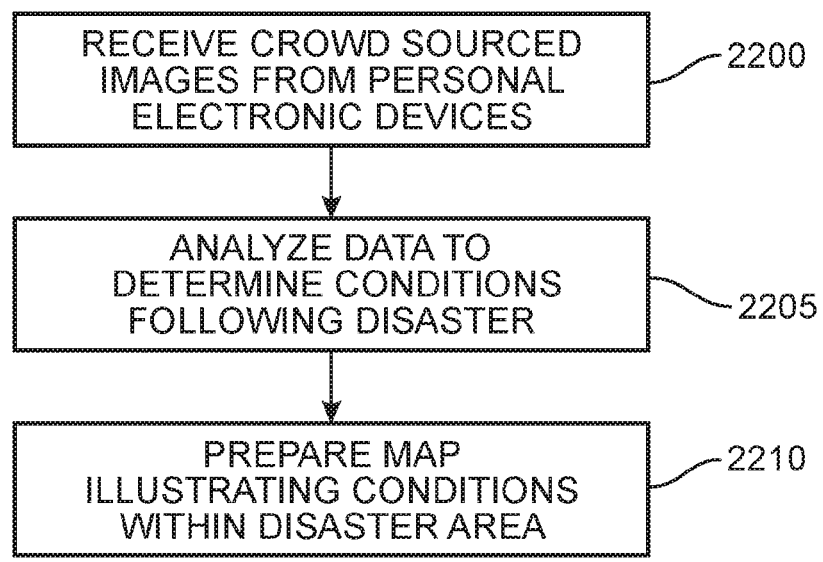
FIG. 22 is a flowchart illustrating another process of analyzing and utilizing crowd sourced images.

FIG. 22 is a flowchart illustrating another process of analyzing and utilizing crowd sourced images. As shown in FIG. 22, the computer readable medium may include instructions for receiving crowd sourced images from personal electronic devices (step 2200). In addition, the computer readable medium may include instructions for analyzing the data to determine disaster conditions (step 2205). Further, the computer readable medium may include instructions for preparing a map illustrating the detected conditions in the geographic region (step 2210). The map may include multiple layers of information regarding the determined conditions.

In some embodiments, the system may provide a platform that users may utilize to submit their images for consideration. For example, a website or mobile app may be configured to facilitate uploading images to a conditions monitoring center or other interested party for consideration in determining post-disaster conditions and preparing disaster response strategies.

Figure 23:
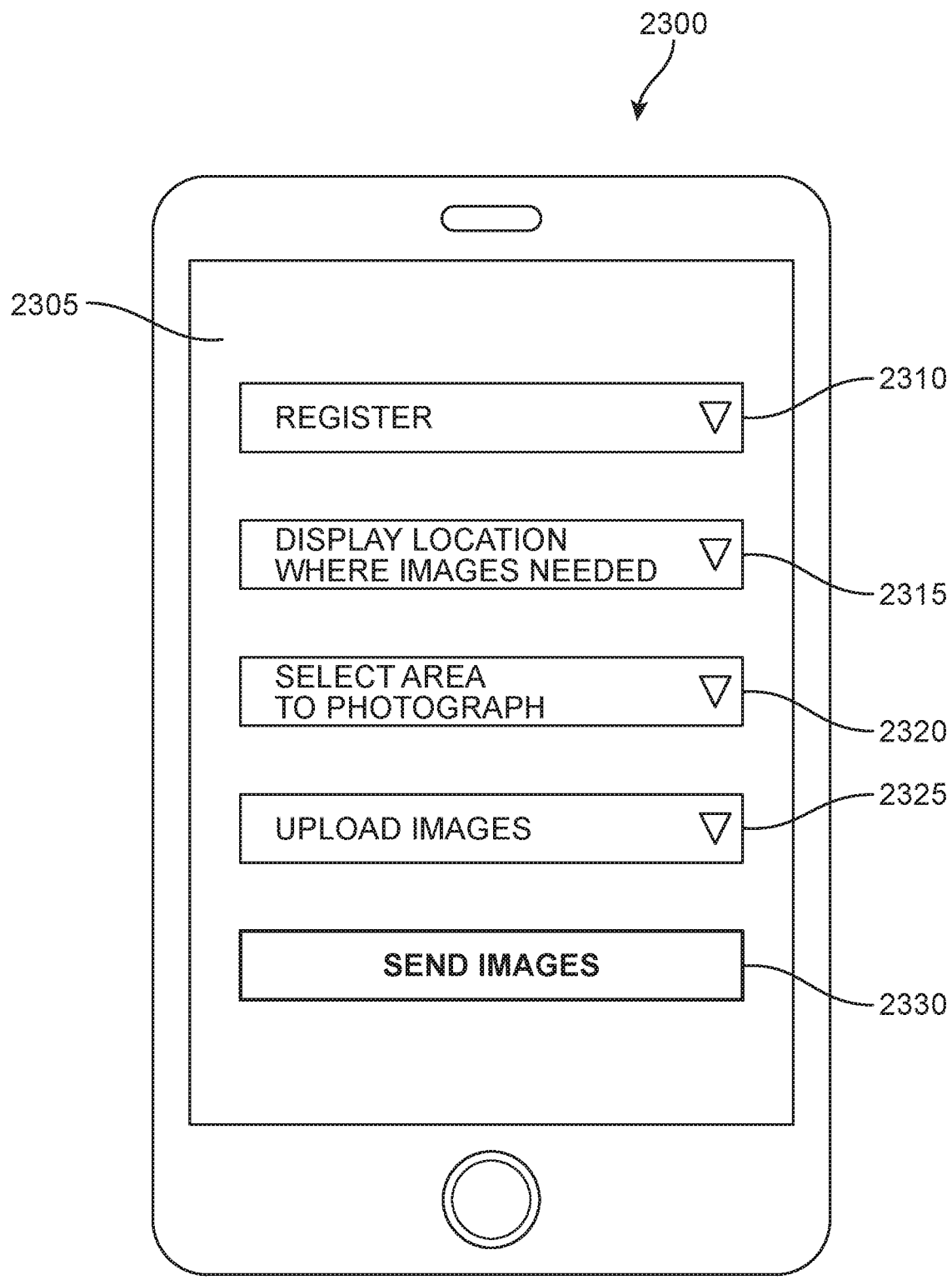
FIG. 23 is a schematic illustration of a portable electronic device showing an app interface for uploading images.

FIG. 23 is a schematic illustration of a portable electronic device showing an app interface for uploading images. FIG. 23 is a schematic illustration of a personal electronic device 2300 displaying a user app. As shown in FIG. 23, personal electronic device 2300 may include a graphical user interface 2305.

Personal electronic device 2300 may include a device processor and a non-transitory computer readable medium including instructions executable by the device processor. These components may have the same or similar attributes discussed above with respect to similar components in other embodiments.

The computer readable medium of device 2300 may include instructions for registering the user with a disaster response system, e.g., via a menu item 2310. In addition, the app may be configured to display locations from which images are needed, e.g., via menu item 2315. By selecting menu item 2315, a map may be displayed illustrating the areas from which images are needed. Such a map may appear similar to map 2000 shown in FIG. 20. The user may be able to select the various areas where images are needed (menu item 2320), to thereby volunteer their services in obtaining and uploading images from the selected locations. Once the images have been captured, the user may upload the images via menu item 2325, and submit or send the images via menu item 2330. For example, the user may send the images to a conditions monitoring center.

In some embodiments, the computer readable medium may include instructions for receiving information regarding disaster conditions from the conditions monitoring center. The computer readable medium may further include instructions for displaying a map including the information received from the conditions monitoring center. The map includes multiple layers of the information received from the conditions monitoring center. In addition, the computer readable medium may include instructions for updating the map including the information regarding locations where images are needed by removing the locations for which the user sent images.

Drones

Drones may be used for several tasks following disasters. On-board cameras and sensors can help collect data. In some cases, fleets of drones may be deployed. The fleets may be pre-assembled, or may be simply collections of volunteer drones assembled after the disaster has occurred. The drones may be auto-controlled. In some cases, the auto-control may operate the drones collectively as a fleet.

A network may be provided to feed the data (e.g., images) captured by the drones back to a centralized location such as a conditions monitoring center. The drones themselves may serve as repeaters to pass along the data. In some cases, dedicated repeaters may be provided on land or on other vehicles such as emergency trucks in the area.

In some cases, other types of robots or drones, such as unmanned land vehicles or watercraft may be used in a similar way as aerial drones. Such land and water vehicles may be useful in disasters such as fires, where smoke prevents the collection of useful imagery from the air. Drones may also be configured to collect air quality or water quality samples and, in some cases, perform testing on such samples.

Figure 24:
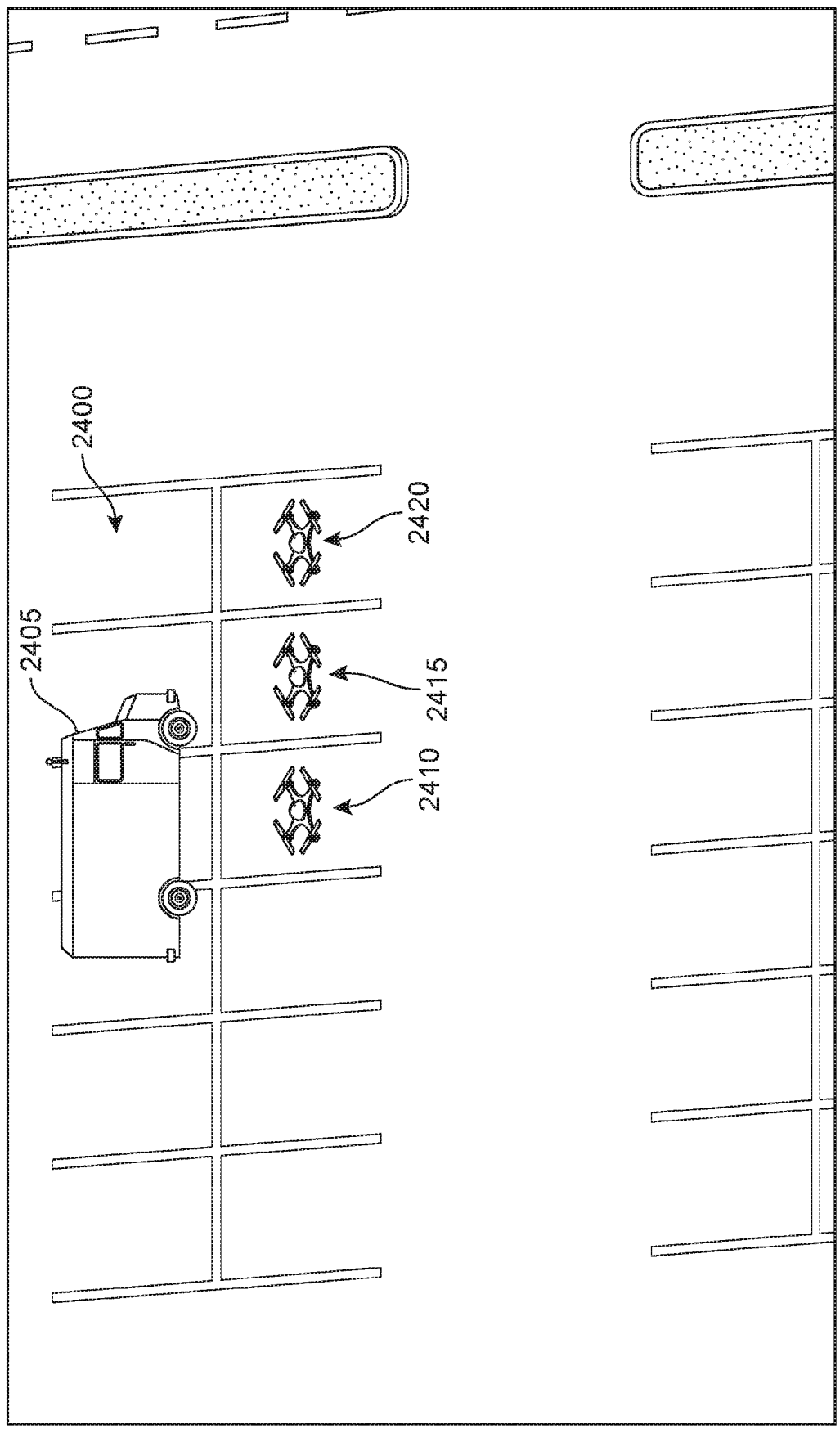
FIG. 24 is a schematic illustration of a post-disaster monitoring system configured to receive images obtained using a fleet of drones.

FIG. 24 is a schematic illustration of a post-disaster monitoring system 2400 configured to receive images obtained using a fleet of drones. As shown in FIG. 24, system 2400 may include a mobile control center in the form of vehicle 2405. In addition, system 2400 may be configured to include and/or be operable in association with a plurality of drones configured to collect information, such as photographic images, of a disaster area. In some cases, the drones may be configured to obtain video recordings. As shown in FIG. 24, a first drone 2410, a second drone 2415, and a third drone 2420 may be dispatched from the mobile control center provided by vehicle 2405. In other cases, a permanent facility, such as a fire station, may be utilized as the control center. Alternatively, the drone fleet may be comprised of a plurality of privately owned drones that are utilized by their respective owners to obtain the imagery. Further, in some embodiments, privately owned drones may be offered by their owners to be utilized by disaster responders to capture images for analysis.

The specifications of the drones associated with system 2400 may be suited for the type of terrain, routes, imagery, data collection, etc. for which the drones are to be used. The drones may have enough power to carry the necessary photography, film, and/or data collection equipment. In some embodiments, such equipment may include various types of photography and/or film equipment, including standard visual, infrared, night vision, and other types of imagery equipment. Infrared imagery may facilitate searches for humans and/or animals in a disaster area, particularly among damaged buildings and other structures. In addition, thermal imagery, such as infrared, may be combined with standard visual images to detect water conditions. Further, in some embodiments, the drones may include other types of data collection equipment such as Light Detection and Ranging (LIDAR), which is a remote sensing system configured to map the surface of the earth, and may penetrate vegetation in order to provide an accurate topographical scan of the ground surface. This may be used to determine structural damage to buildings, roadways, and other infrastructure, as well as ground conditions, such as mudslides, flooding, extreme erosion, etc. Additionally, or alternatively, the drones may include air quality sensors, water quality sensors, or other data collection devices.

In addition, the drones may have enough range, both in terms of controllability/navigation and battery life in order to travel the required distance to the location to be photographed. For example, drones may be configured with capability to fly from an edge of a disaster area to locations that are centrally located within the disaster area. In some cases, the drones may be capable of flying from an edge of a disaster area to an opposite edge of the disaster area. For example, if a disaster area falls along a coastline or lake, the shoreline may form the edge of the disaster area on one side. Accordingly, the closest a drone may be deployed to the location to be photographed may be the opposite edge of the disaster area. Accordingly, the drones may be capable of traversing the full distance across the disaster area to complete certain reconnaissance missions. The system may be configured to dispatch the drones according to the specifications of each drone.

Further, the communication capabilities shall also be duly suited for each drone's intended use. In some embodiments, the drones may be autonomous. That is, the drones may be programmable to execute imaging runs to designated locations. In other embodiments, the drones may be piloted remotely.

Any suitable system may be utilized for video and/or audio communication. For example, radio, satellite, cellular, Internet, or other communication networks may be utilized.

Figure 25:
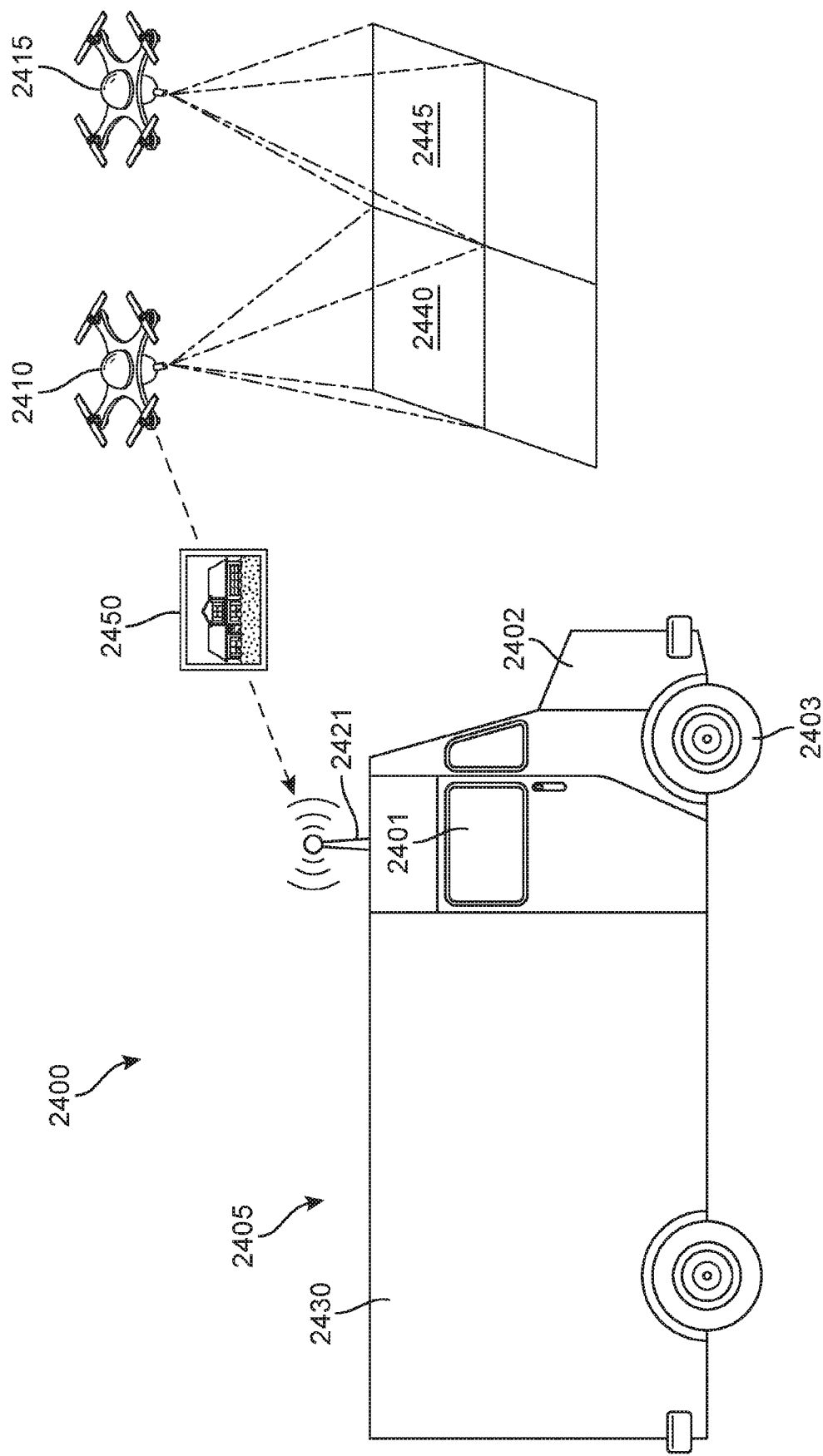
FIG. 25 is a schematic illustration of a the system shown in FIG. 24 with the drones airborne and collecting images.

FIG. 25 is a schematic illustration of the system shown in FIG. 24 with the drones airborn and collecting images. The conditions monitoring center, be it housed in vehicle 2405 or elsewhere, may include a controller including a device processor and a non-transitory computer readable medium including instructions executable by the device processor.

In particular, the computer readable medium may include instructions for receiving images from the plurality of aircraft drones in a geographic region; and determining conditions in the geographic region based on the images received from the plurality of aircraft drones.

As shown in FIG. 25, vehicle 2405 may include basic components of a vehicle, such as a power source 2402, wheels 2403, a driver's cab 2401, etc. In addition, vehicle 2405 may also include an equipment compartment 2430 configured to house condition monitoring equipment, disaster relief supplies, etc. Also, vehicle 2405 may include drone communication equipment, such as an antenna 2421 and one or more associated transmitters, receivers, and/or transceivers.

As shown in FIG. 25, the drones may be operated to photograph different areas of a geographic region, such as a disaster area. For example, as shown in FIG. 25, first drone 2410 may be operated to photograph a first area 2440 and second drone 2425 may be operated to photograph a second area 2445. The photographic images of these areas may then be transmitted back to the control center. For example, as shown in FIG. 25, in some embodiments, the drones may send the images back to vehicle 2405, as illustrated by image 2450 in FIG. 25.

The photographs may be processed by the system to assess the conditions in the disaster area. In addition, the system may be configured to send information regarding the determined conditions to one or more users of the system. In some embodiments, the computer readable medium of the system may include instructions for preparing a map indicating the determined conditions within the geographic region. In some cases, the map may include multiple layers of information. In some embodiments, one or more of the layers of information may include information regarding population density in the geographic region.

Figure 26:
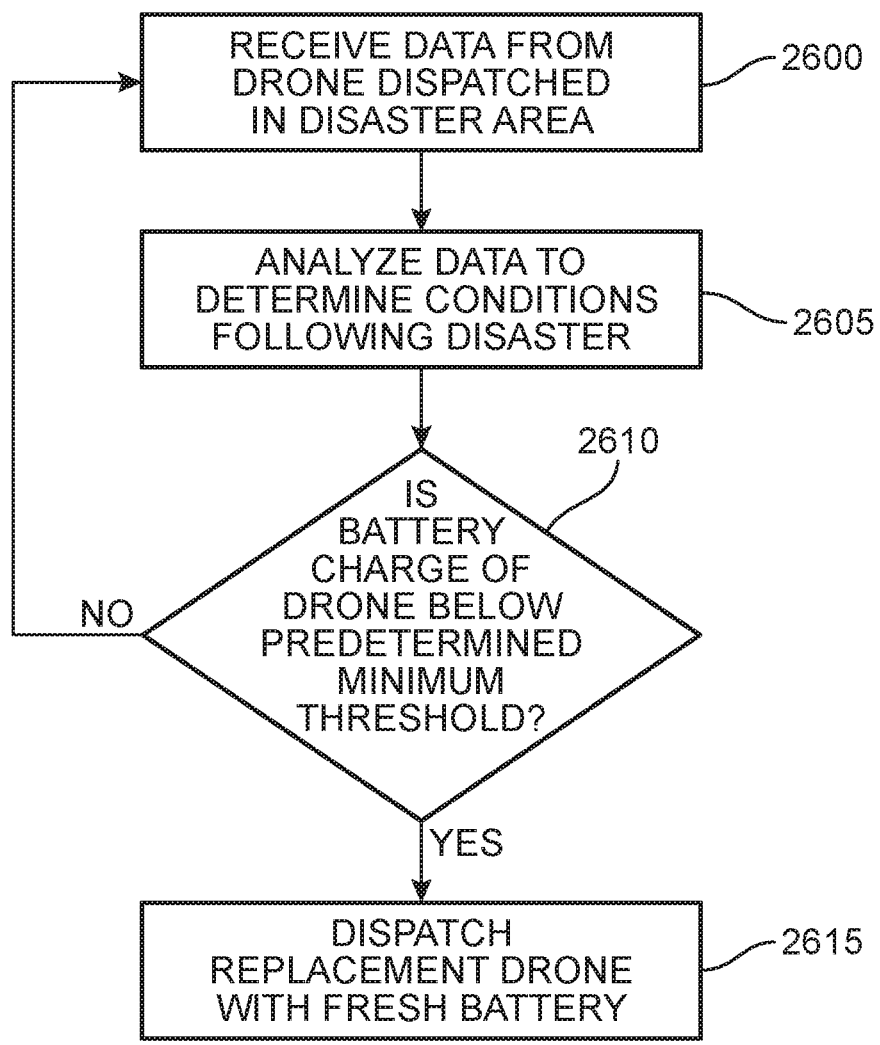
FIG. 26 is a flowchart illustrating a process of dispatching drones for capturing images on an ongoing basis.

FIG. 26 is a flowchart illustrating a process of dispatching drones for capturing images on an ongoing basis. As shown in FIG. 26, the computer readable medium of a post-disaster monitoring system may include instructions for receiving data from one or more drones dispatched in a disaster area (step 2600). In addition, the computer readable medium may include instructions for analyzing the data to determine conditions in the disaster area following the disaster (step 2605).

In some embodiments, the computer readable medium may include instructions for determining whether the battery charge of a dispatched drone is below a predetermined threshold (step 2610). If not, the system may continue to receive data from the drone as it captures additional images, as indicated by the return of the process to step 2600 in FIG. 26. If the battery charge is detected as having dropped below the predetermined threshold (at step 2610), the system may dispatch a replacement drone with a fresh battery (step 2615). In some cases, the system may recall the originally dispatched drone to the dispatch location. In some cases, the original drone may be recharged at the dispatch location or elsewhere, and then readied for further deployment.

In some cases, the system may be configured for the drones to send the images back to a control center without having to physically return to the center for download of the images. In some cases, the system may be configured to utilize one or more repeaters to relay the delivery of imaging data from the drones to the control center. In some cases, one or more of the drones may be configured to relay data from other drones to the control center. In some cases, a land vehicle, such as vehicle 2405 may be configured to relay the data to a condition monitoring center or other facility.

Figure 27:
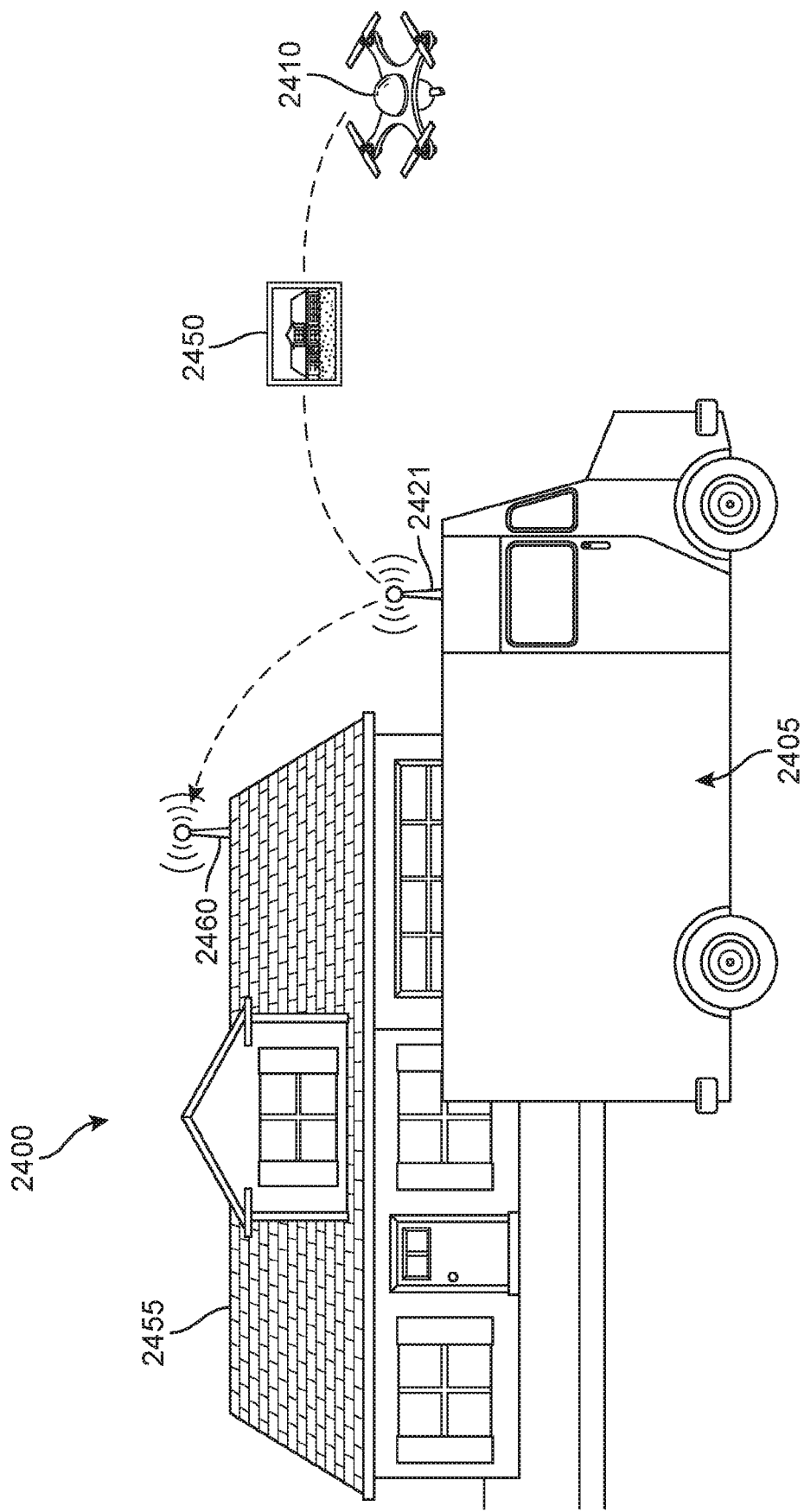
FIG. 27 is a schematic illustration of a post-disaster monitoring system including at least one signal repeater deployed on a vehicle.

FIG. 27 is a schematic illustration of a post-disaster monitoring system including at least one signal repeater deployed on a vehicle. As shown in FIG. 27, image 2450 may be sent by first drone 2410 to vehicle 2405 and relayed to a condition monitoring center 2455 located remote from vehicle 2405. Condition monitoring center 2455 may include communications equipment to receive such relayed communications, as indicated by an antenna 2460.

The system may include a platform, such as a website or app, with which drone owners can volunteer the services of their personally owned drone. Through the app, the users can obtain an assignment to complete a reconnaissance mission using their drone. Such a platform may facilitate the organization of a large number of drones to photograph a disaster area without needing a large fleet of dedicated disaster response drones to be owned and operated by disaster relief organizations.

Figure 28:
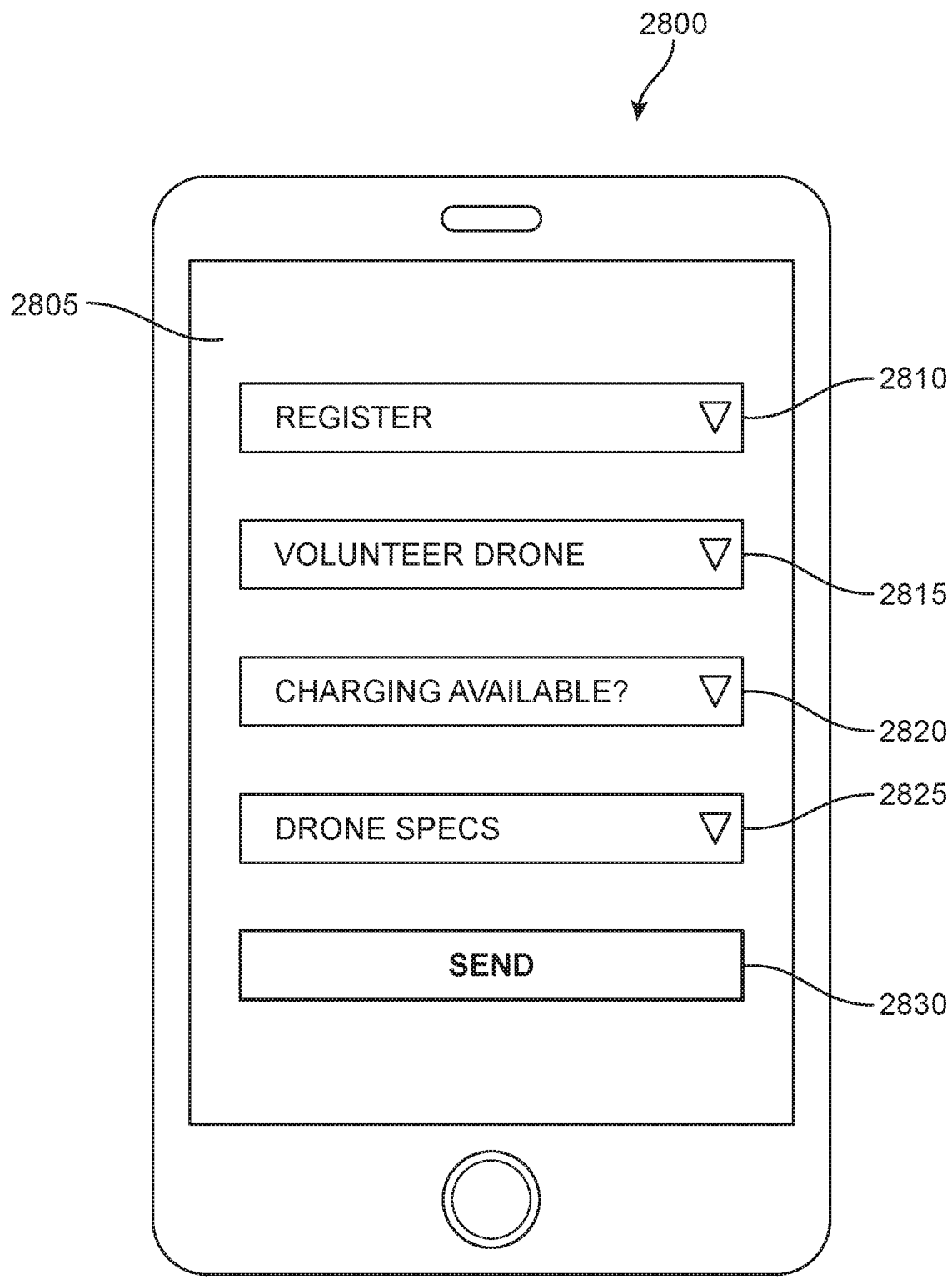
FIG. 28 is a schematic illustration of a portable electronic device showing an app interface for volunteering use of a personal drone.

FIG. 28 is a schematic illustration of a portable electronic device showing an app interface for users to volunteer the services of their personally owned drone. FIG. 28 is a schematic illustration of a personal electronic device 2800 displaying a user app. As shown in FIG. 28, personal electronic device 2800 may include a graphical user interface 2805.

Personal electronic device 2800 may include a device processor and a non-transitory computer readable medium including instructions executable by the device processor. These components may have the same or similar attributes discussed above with respect to similar components in other embodiments.

The computer readable medium of device 2800 may include instructions for registering the user with a disaster response system, e.g., via a menu item 2810. In addition, the app may be configured to indicate, e.g., via menu item 2815, that they have a drone the services of which they are willing to volunteer for disaster relief purposes. By selecting menu item 2815, a map may be displayed illustrating the areas from which images are needed. Such a map may appear similar to map 2000 shown in FIG. 20. The user may be able to select the various areas where images are needed, to thereby volunteer their services in obtaining and uploading images from the selected locations. The user may also be able to select whether they are offering the use of their drone to disaster response organizations or if they will operate their drone themselves.

The user may also indicate, via a menu item 2820 whether they have battery charging services available that they are willing to share with other drone operators. In addition, the user may utilize menu item 2825 to select various specifications of their drone, in order to ensure that the system assigns a reconnaissance mission that is suitable for the capabilities of the volunteer's drone. For example, the user may select whether their drone is remotely operated or programmable/autonomous. The computer readable medium of device 2800 may include instructions for executing the tasks described above. In addition, the computer readable medium may also include instructions for uploading images taken during the volunteer drone service. The image upload feature may be executed according to the description above with respect to FIG. 23.

Figure 29:
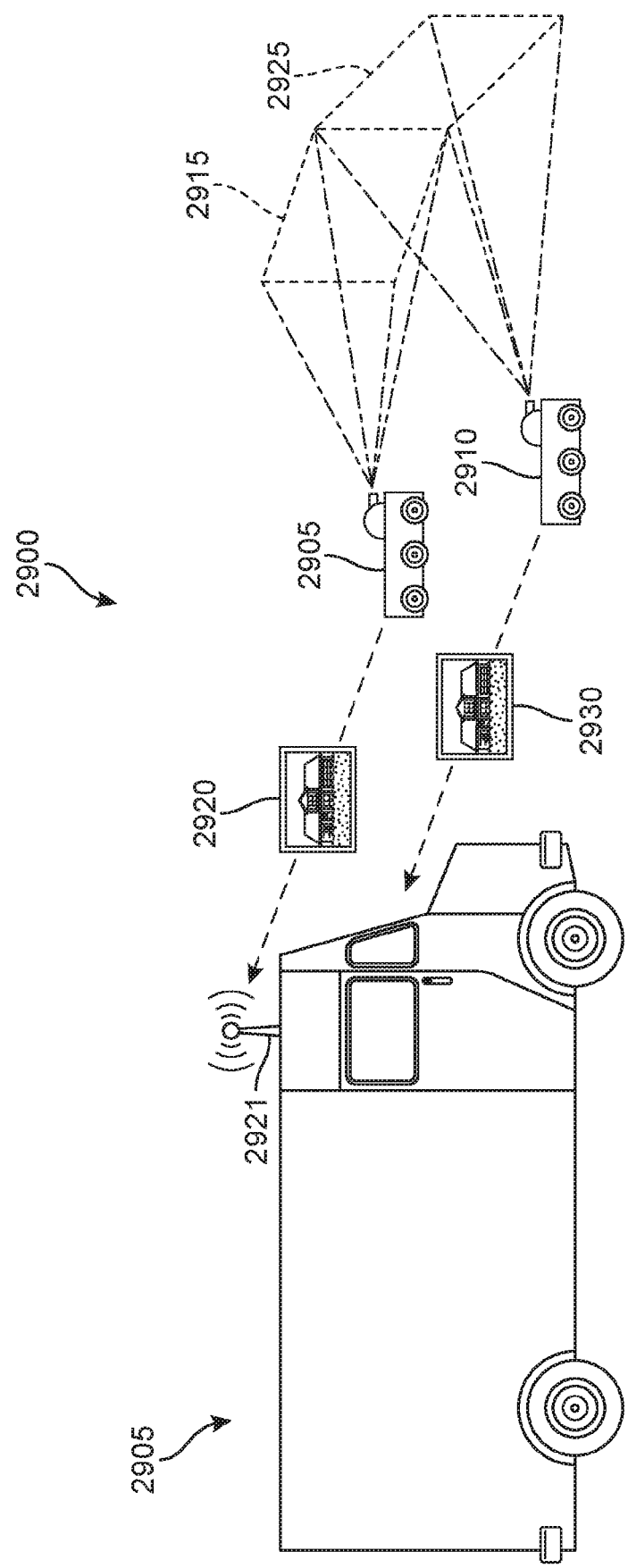
FIG. 29 is a schematic illustration of a post-disaster monitoring system including a plurality of land vehicles.

In some embodiments, land vehicle drones and/or watercraft drones may be utilized in a similar manner as described above with respect to aerial drones. FIG. 29 is a schematic illustration of a post-disaster monitoring system 2900 including a plurality of land vehicles. As shown in FIG. 29, system 2900 may include a control center, such as a vehicle 2905. Control center vehicle 2905 may have features and capabilities that are the same or similar to those described above with respect vehicle 2405 in FIG. 25.

System 2900 may also include a plurality of land vehicle drones, such as a first drone 2905 and a second drone 2910. In some embodiments, these drones may be operated remotely. In some embodiments, these drones may be operated autonomously. Further, in some embodiments, these drones may be equipped with air quality sensors. Such sensors may be usable to determine the conditions in various disaster situations, such as a fire with voluminous smoke, or a chemical plant explosion, where there may be dangerous aerosols in the air.

In some embodiments, the drones may include photography equipment for acquiring images of a disaster area. Such ground-based drones may be useful in obtaining images in situations like fires where the smoke may limit the effectiveness of aerial imagery. As shown in FIG. 29, first drone 2905 may be utilized to photograph a first area 2915 and send the images 2920 back to the control center. In addition, second drone 2910 may be utilized to photograph a second area 2925 and send the images 2930 back to the control center.

The control center or conditions monitoring center may include having a controller including a device processor and a non-transitory computer readable medium including instructions executable by the device processor to receiving data from the air quality sensors or photography equipment and determine conditions in a geographic region based on the received data. In addition, the computer readable medium may include instructions for sending information regarding the determined conditions to one or more users of the system.

Figure 30:
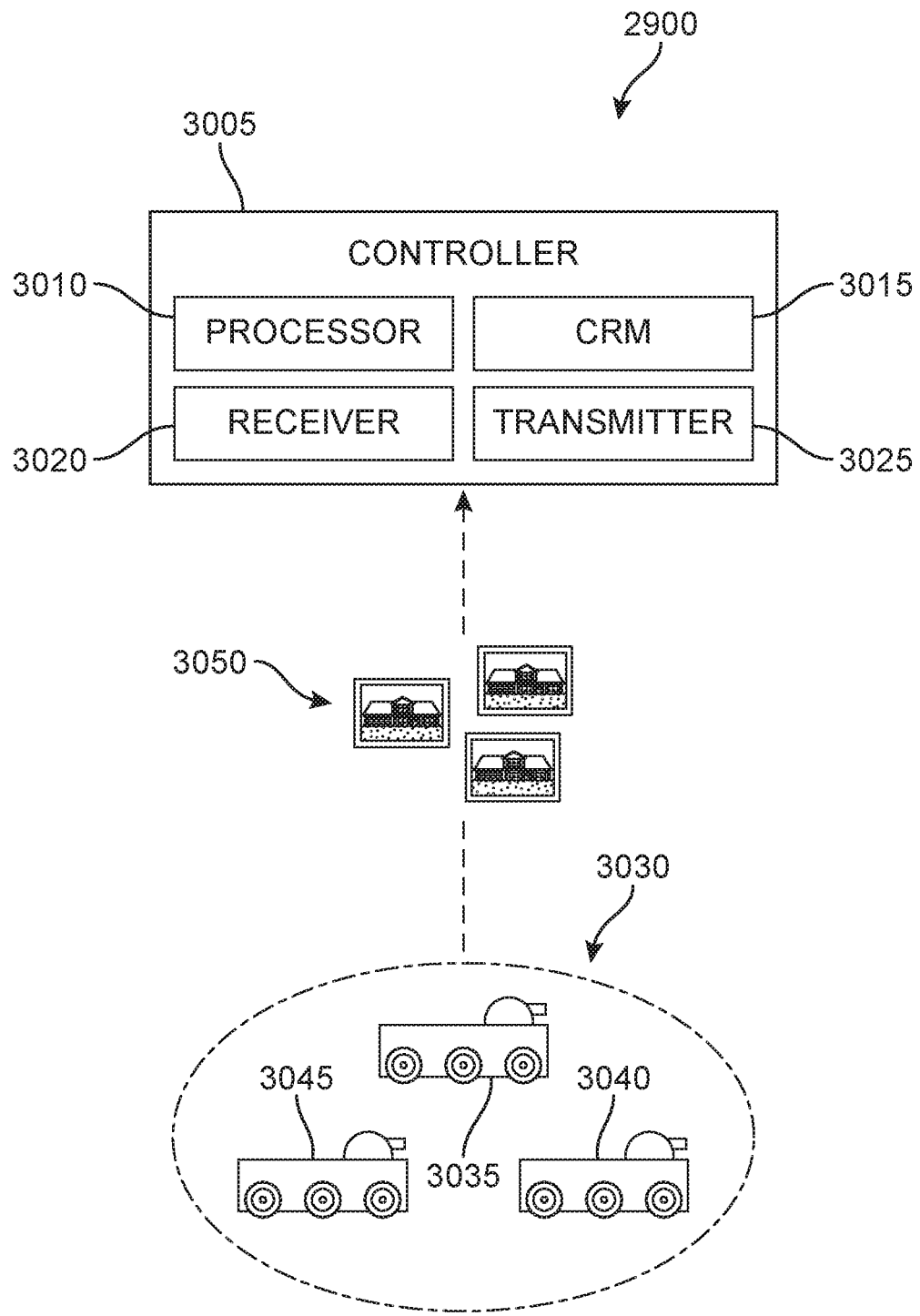
FIG. 30 is a schematic illustration of components of the system shown in FIG. 29.

FIG. 30 is a schematic illustration of components of the system shown in FIG. 29. As shown in FIG. 30, system 2900 may include a controller 3005. Controller 3005 may include various computing and communications hardware, such as servers, integrated circuits, displays, etc. Further, controller 3005 may include a device processor 3010 and a non-transitory computer readable medium 3015 including instructions executable by device processor 3010 to perform the processes discussed herein. The components of controller 3005 may be implemented in association with a mobile conditions monitoring center, such as vehicle 2905, or in association with a control center or conditions monitoring center located in a permanent building (i.e., brick and mortar establishment). Controller 3005 and its components may have the same or similar features as controller 105 and its components discussed above.

As shown in FIG. 30, a fleet 3030 of drones, including a first drone 3035, a second drone 3040, and a third drone 3045 may acquire a plurality of photographic images 3050. These images 3050 may be sent back to controller 3005. Computer readable medium 3015 may include instructions for receiving images 3050 and determining conditions in the photographed area based on images 3050.

The embodiments discussed herein may make use of methods and systems in artificial intelligence to improve efficiency and effectiveness of the disclosed systems. As used herein, "artificial intelligence" may include any known methods in machine learning and related fields. As examples, artificial intelligence may include systems and methods used in deep learning and machine vision.

While various embodiments have been described, the description is intended to be exemplary, rather than limiting, and it will be apparent to those of ordinary skill in the art that many more embodiments and implementations are possible that are within the scope of the embodiments. Although many possible combinations of features are shown in the accompanying figures and discussed in this detailed description, many other combinations of the disclosed features are possible. Any feature of any embodiment may be used in combination with, or substituted for, any other feature or element in any other embodiment unless specifically restricted. Therefore, it will be understood that any of the features shown and/or discussed in the present disclosure may be implemented together in any suitable combination. Accordingly, the embodiments are not to be restricted except in light of the attached claims and their equivalents. Also, various modifications and changes may be made within the scope of the attached claims.

We claim:

1. A method comprising:
    receiving information from a plurality of sensors including a personal electronic device associated with a user, wherein the information is indicative of one or more contaminants present in water within a geographic region;
    determining, using the information, a characterization of the one or more contaminants present in the water within the geographic region;
    preparing a map including at least one selectable layer indicating a location of the one or more contaminants present in the water in the geographic region; and
    sending the characterization of the one or more contaminants present in the water within the geographic region to the personal electronic device associated with the user, wherein sending the characterization of the one or more contaminants present in the water comprises communicating the map to the personal electronic device associated with the user, and facilitating the personal electronic device to display a selected layer of the map.

2. The method of claim 1, wherein the information indicative of the one or more contaminants present in the water includes information regarding at least one of an organic pollutant and a chemical pollutant.

3. The method of claim 1, wherein sending the characterization of the one or more contaminants present in water includes sending the characterization to a plurality of devices associated with respective users.

4. The method of claim 1, wherein the information indicative of the one or more contaminants present in the water includes information regarding a presence of one or more predetermined types of animals.

5. The method of claim 1, wherein the plurality of sensors include one or more disposable sensors and the method further comprises receiving the information indicative of the one or more contaminants present in the water from the one or more disposable sensors.

6. The method of claim 1, wherein the plurality of sensors include one or more Internet of Things sensors and the method further comprises receiving the information indicative of the one or more contaminants present in the water from the one or more Internet of Things sensors.

7. The method of claim 1, wherein preparing the map including the at least one selectable layer indicating the location of the one or more contaminants present in the water in the geographic region comprises providing a symbol in the at least one selectable layer indicating at least one of a condition of the water in the geographic region and a population density in the geographic region.

8. A method comprising:
    receiving information from a plurality of sensors including a personal electronic device associated with a user, wherein the information is indicative of one or more contaminants in water within a geographic region;

determining, using the information, a characterization of the one or more contaminants in the water within the geographic region;

preparing a map indicating a location of the one or more contaminants in the water and the characterization within the geographic region; and sending the map to the personal electronic device associated with the user causing the personal electronic device to display the map.

9. The method of claim 8, wherein the information indicative of the one or more contaminants in the water includes information regarding at least one of an organic pollutant and a chemical pollutant.

10. The method of claim 8, wherein sending the map to the personal electronic device associated with the user facilitates the personal electronic device to display the map.

11. The method of claim 8, wherein the information indicative of the one or more contaminants in the water includes information regarding a presence of one or more predetermined types of animals in the water.

12. The method of claim 8, wherein the plurality of sensors include one or more disposable sensors and the method further comprises receiving the information indicative of the one or more contaminants in the water from the one or more disposable sensors.

13. The method of claim 8, wherein the plurality of sensors include one or more Internet of Things sensors and the method further comprises receiving the information indicative of the one or more contaminants in the water from the one or more Internet of Things sensors.

14. A method comprising:

receiving information from a plurality of sensors including a personal electronic device associated with a user, wherein the information is indicative of one or more contaminants present in a body of water within a geographic region;

determining, using the information, a characterization of the one or more contaminants present in the body of water within the geographic region;

preparing a map including at least one selectable layer indicating a location of the one or more contaminants present in the body of water in the geographic region; and sending the characterization of the one or more contaminants present in the body of water within the geographic region to the personal electronic device associated with the user, wherein sending the characterization of the one or more contaminants present in the body of water comprises communicating the map to the personal electronic device associated with the user, and facilitating the personal electronic device to display a selected layer of the map.

15. The method of claim 14, wherein the information indicative of the one or more contaminants present in the body of water includes information regarding at least one of an organic pollutant and a chemical pollutant.

16. The method of claim 14, wherein sending the characterization of the one or more contaminants present in the body of water to the personal electronic device associated with the user facilitates the personal electronic device to display the characterization.

17. The method of claim 14, wherein the information indicative of the one or more contaminants present in the body of water includes information regarding one or more predetermined types of animals.

18. The method of claim 14, wherein the plurality of sensors include one or more disposable sensors and the method further comprises receiving the information indicative of the one or more contaminants present in the body of water from one or more disposable sensors.

19. The method of claim 14, wherein the body of water is flood water.

20. The method of claim 14, wherein the body of water is a pre-existing body of water.

* * * * *